(12) United States Patent
Burton et al.

(10) Patent No.: US 8,728,493 B2
(45) Date of Patent: May 20, 2014

(54) POLYMER BASED COMPOSITIONS AND CONJUGATES OF NON-STEROIDAL ANTI-INFLAMMATORY DRUGS

(75) Inventors: Kevin Burton, Madison, AL (US); Xuan Zhao, Dong Cheng District (CN); Michael Bentley, Hunstville, AL (US)

(73) Assignee: Nektar Therapeutics, San Francisco, CA (US)

( * ) Notice: Subject to any disclaimer, the term of this patent is extended or adjusted under 35 U.S.C. 154(b) by 2107 days.

(21) Appl. No.: 11/454,998

(22) Filed: Jun. 15, 2006

(65) Prior Publication Data

US 2007/0025956 A1 Feb. 1, 2007

Related U.S. Application Data

(60) Provisional application No. 60/691,846, filed on Jun. 17, 2005.

(51) Int. Cl.
*A61K 9/00* (2006.01)
*A01N 43/38* (2006.01)
*A61K 31/40* (2006.01)

(52) U.S. Cl.
USPC .......................................... 424/400; 514/412

(58) Field of Classification Search
USPC .......................................... 424/400; 514/412
See application file for complete search history.

(56) References Cited

U.S. PATENT DOCUMENTS

| | | | |
|---|---|---|---|
| 5,932,462 A | 8/1999 | Harris et al. | |
| 6,108,033 A | 8/2000 | Ito et al. | |
| 6,348,558 B1 | 2/2002 | Harris et al. | |
| 6,362,254 B2 | 3/2002 | Harris et al. | |
| 6,514,491 B1 | 2/2003 | Bentley et al. | |
| 6,602,975 B2 | 8/2003 | Hubbell et al. | |
| 6,730,334 B2 | 5/2004 | Zhao | |
| 2003/0082345 A1 | 5/2003 | Hamilton et al. | |
| 2005/0009988 A1 | 1/2005 | Harris et al. | |

FOREIGN PATENT DOCUMENTS

| | | |
|---|---|---|
| WO | WO-2004/006967 A1 | 1/2004 |
| WO | WO-2004/060977 A1 | 7/2004 |
| WO | WO-2004/089420 A1 | 10/2004 |
| WO | WO-2005/000360 A2 | 1/2005 |
| WO | WO-2005/028539 A2 | 3/2005 |

OTHER PUBLICATIONS

Jung et al (Eur J Clin Pharmacol (1988) 35:423-425).*
Anderson, G.W., et al., "The Use of Esters of N-Hydroxysuccinimide in Peptide Synthesis", *J. Am. Chem. Soc.*, 86:1839-1842 1964.
Barlos, K., et al., "Crystal Structure of 3-($N^{\alpha}$-Tritylmethionyl)benzotriazole 1-Oxide, a Synthon in Peptide Synthesis", *J. Org. Chem.*, 50:696-697 (1985).
Castro, B., et al., Reactifs De Couplage Peptidique IV (1)—L'Hexaflurophosphate De Benzotriazolyl N-Oxytrisoimethylamino Phosphonium (B.O.P), *Tetrahedron Letters*, 14:1219-1222 (No English Translation Available)(1975).

(Continued)

*Primary Examiner* — Benjamin Packard
(74) *Attorney, Agent, or Firm* — Timothy A. Marquart

(57) ABSTRACT

Provided herein are water-soluble polymer conjugates and polymer-based compositions of non-steroidal anti-inflammatory drugs. Also provided are methods for synthesizing and administering such conjugates and compositions.

16 Claims, 1 Drawing Sheet

(56) References Cited

OTHER PUBLICATIONS

Davies, G., et al., "Cyclooxygenase-2 (COX-2), Aromatase and Breast Cancer: A Possible Role for COX-2 Inhibitors in Breast Cancer Chemoprevention", *Annals of Oncology*, 13:669-678 (2002).
Duncan, Ruth, "Nanomedicines in Action" *The Pharmaceutical Journal*, 273:485-488 (2004).
Fries et al. *Clinical Significance and Potential of Selective Cox-2 Inhibitors*, "The Clinical Epidemiology of Non-Steroidal Anti-Inflammatory Drug Gastropathy", William Harvey Press (London) Chapter 6, 57-64 (1998).
Harris, J. M., Ed., Topics in Applied Chemistry, *Poly(Ethylene Glycol) Chemistry*, "Introduction to Biotechnical and Biomedical Applications of Poly(ethylene Glycol)", Chapter 1, pp. 1-14, Plenum Press, NY, (1992).
Kato, M., et al., "Cyclooxygenase-1 and Cyclooxygenase-2 Selectivity of Non-Steroidal Anti-Inflammatory Drugs: Investigation Using Human Peripheral Monocytes", *Journal of Pharmacy and Pharmacology*; 53(12):1679-1685 (2001).
König, W., and Geiger, R. "Eine neue Methods Zur Synthese Von Peptiden: Aktivierung der Carboxylgrupe mit Dicyclohexylcarbodiimid unter Zusatz von 1-Hydroxy-Benzotriazlolen" *Chem. Ber.*, 103:788-798 (No English Translation of Article Available, English Abstract provided)(1970).
König, W., and Geiger, R., "N-Hydroxyverbindungen als Katalysatoren für die Aminolyse Aktivierter Ester", *Chem. Ber.*, 106:3626-3635 (No English Translation of Article Available, English Abstract provided) (1973).
Koki et al., "Potential Utility of COX-2 Inhibitors in Chemoprevention and Chemotherapy" *Expert Opinion Investig. Drugs*, 8:1623-1638 (1999).
Leach, J. B., et al., "Development of photocrosslinkable hyaluronic acid-polyethylene glycol-peptide composite hydrogels for soft tissue engineering", Wiley InterScience, May 13, 2004 (published online), *J. Biomed Mater Res.*, 70A:74-82 (2004).
Li, J., "Synthesis of Polyethyleneglycols (PEGs): Derivatives and Applications in Biomaterials", Jing Li, BME 430, 5 pages (May 2003).
Mehanna, A.S., "Teacger Topics, NSAIDs: Chemistry and Pharmacological Actions", *American Journal of Pharmaceutical Education*, 67(2):Article 63, pp. 1-7, (2003).
Ogura, H., et al., "A Novel Active Ester Synthesis Reagent (N,N-Disuccinimidyl Carbonates)", *Tetrahedron Letters*, 49:4745-4746 (1979).
Ogura, H., et al., "β-Elimination of β-Hydoxyamino Acids with Disuccinimido Carbonate", *Tetrahedron Letters*, 49:4817-4818 (1981).
Ouchi et al., Polymer Preprints, American Chemical Society, "Design of Antitumor Agent-Terminated Poly(Ethylene Glycol) Conjugate as Macromolecular Prodrug", 38(1):582-583 (1997).
Pasut, G. et al., "Protein, Peptide and Non-Peptide Drug Pegylation for Therapeutic Application", *Expert Opin. Ther. Patents*, 14(6):859-894 (2004).
Quadir et al., "Development and Evaluation of Nasal Formulations of Ketorolac", *Drug Delivery*, 7(4):223-229 (2000).
Reddy, B S et al., "Chemoprevention of Colon Cancer by Specific Cyclooxygenase-2 Inhibitor, Celecoxib, Administered During Different Stages of Carcinogenesis", *Cancer Research*, 60:293-297 (2000).
Roberts, M. et al., "Chemistry for Peptide and Protein PEGylation", *Advanced Drug Delivery Reviews*, 54:459-476 (2002).
Roy et al., "Transdermal Delivery of Ketorolac Tromethamine: Permeation Enhancement, Device Design, and Pharmacokinetics in Healthy Humans", *Journal of Pharmaceutical Sciences*, 84(10):1190-1196 (1995).
Takeda, K., et al., "An Improved Method for the Synthesis of Active Esters of N-Protected Amino Acids and Subsequent Synthesis of Dipeptides", *Synthesis*, pages 689-691 (1991).

Tiwari et al., "Investigation into the Potential of Iontophoresis Facilitated Delivery of Ketorolac", *International Journal of Pharmaceutics*, 260(1):93-103 (2003).
Veronese, F. M., Morpurgo, M., "Bioconjugation in Pharmaceutical Chemistry", *Il Farmaco*, 54(8):497-516 (1999).
Weygand, F., et al., "Peptidsynthesen Mit Dicyclohexylcarbodiimid unter Zusatz von N-Hydroxysuccinimid", *Z. Naturforschg.*, 21 b:426-428 (1966).
Wong, S. S., Ed. "Chemistry of Protein Conjugation and Cross-Linking", Chapter 3, pp. 49-73, CRC Press, Boca Raton, Fla., (1991).
Zalipsky, S., "Chemistry of Polyethylene Glycol Conjugates with Biologically Active Molecules", *Advanced Drug Reviews*, 16:157-182 (1995).
Zalipsky, Samuel, et al., "Use of Functionalized Poly(Ethylene Glycols) for Modification of Polypeptides" in Polyethylene Glycol Chemistry, Chapter 21, pp. 347-370, Biotechnical and Biomedical Applications, J. M. Harris, Plenum Press, New York (1992).
Zalipsky, Samuel, "Functionalized Poly(ethylene Glycol) for Preparation of Biologically Relevant Conjugates", *Bioconjugate Chemistry*, 6:150-165 (1995).
Zalipsky, Samuel, "Attachment of Drugs to Polyethylene Glycols", *Eur. Polym. J.*, 19(12):1177-1183 (1995).
Enzon Pharmaceuticals Catalog, "Macromolecular Engineering Technologies," pp. 1-14 (2004).
Nektar Molecule Engineering Catalog, "Polyethylene Glycol and Derivatives for Advanced PEGylation," pp. 1-21 (2003).
Nektar Advanced PEGylation Catalog, "Polyethylene Glycol and Derivatives for Advanced PEGylation," pp. 1-24 (2004).
Nektar Advanced PEGylation Catalog, "Polyethylene Glycol and Derivatives for Advanced PEGylation," pp. 1-30 (2005-2006).
NOF Corporation Catalog, "Peg Derivatives, Phospholipid and Drug Delivery Materials for Pharmaceuticals," 1: pp. 2-46 (2003).
Polypure Products Catalog, Apr. 2005.
Quanta Biodesign Catalog, "Labeling, Modification and Crosslinking Reagents Incorporating our Unique Monodispersed dPEG™ Technology," pp. 1-38, Mar. 12, 2004.
Quanta Biodesign Catalog, "Labeling, Derivatization and Crosslinking Reagents for Biological and Related Materials with dPEG," pp. 1-31, Nov. 5, 2004.
Quanta Biodesign Product Catalog, "Leading Innovator, Producer and Provider of Monodisperse Discrete PEG (dPEG) Derivatives," pp. 1-51, Nov. 17, 2005.
Shearwater Polymers, Inc., Catalog, "Functionalized Biocompatible Polymers for Research: Polyethylene Glycol and Derivatives," pp. 2-49 (Mar. 1995).
Shearwater Polymers, Inc., Catalog, "Functionalized Biocompatible Polymers for Research and Pharmaceuticals: Polyethylene Glycol and Derivatives," pp. 2-53 (1997-1998).
Shearwater Polymers, Inc., Catalog, "Functionalized Biocompatible Polymers for Research and Pharmaceuticals: Polyethylene Glycol and Derivatives," pp. 2-50 (2000).
Cecchi, R., et al., "Synthesis and Pharmacological Evaluation of Poly(Oxyethylene) Derivatives of 4-Isobutylphenyl-2-Propionic Acid (Ibuprofen)", *J. Med. Chem.*, 24:622-625 (1981).
The Partial International Search Report and Invitation to Pay Additional Fees for PCT/US2006/023307, Search report dated Mar. 26, 2008, 12 pages (2008).
Davaran, S., et al., "Synthesis and Hydrolytic Behavior of 2-Mercaptoethyl Ibuprofenate-Polyethylene Glycol Conjugate as a Novel Transdermal Prodrug", *Pharmacy and Pharmacology*, 55:513-517 (2003).
Hoste, K. et al., "Polymeric Prodrugs", *International Journal of Pharmaceutics*, 277:119-131 (2004).
Jiang, H., et al., "Preparation and Characterization of Ibuprofen-Loaded Poly(lactide-*co*-glycolide)/poly(ethylene glycol)-*g*-chitosan Electrospun Membranes", *J. Biomater. Sci. Polymer Edn.*, 15(3):279-296 (2004).
Kolhe, P. et al., "Hyperbranched Polymer-Drug Conjugates with High Drug Payload for Enhanced Cellular Delivery", *Pharmaceutical Research,*, 21(12):2185-2195 (2004).

(56) References Cited

OTHER PUBLICATIONS

Lele, B.S., and Hoffman, A.S., "Mucoadhesive Drug Carriers Based on Complexes of Poly(acrylic acid) and PEGylated Drugs Having Hydrolysable PEG-Anhydride-Drug Linkages", *Journal of Controlled Release*, 69:237-248 (2000).

NOF Corporation Catalog, "Peg Derivatives, Phospholipid and Drug Delivery Materials for Pharmaceuticals Products and Formulations," pp. 1-59 (2006).

NOF Corporation Website, "PEGylation and Activated PEGs," Retrieved from NOF website Dec. 12, 2006, 9 pages, (2006).

Polypure Products Catalog, 5 pages, Apr. 2004.

Shearwater Corporation, "Polyethylene Glycol and Derivatives for Biomedical Applications," pp. 1-17 (2001).

Notification of Transmittal of the International Search Report and the Written Opinion of the International Searching Authority, or the Declaration, mailed on Jul. 1, 2008, corresponding to PCT Application No. PCT/US2006/023307.

International Preliminary Examination Report, mailed on Jul. 24, 2008, corresponding to PCT Application No. PCT/US2006/023307.

European Office Action dated Oct. 28, 2008, corresponding to European Application No. 06 773 243.8-1216.

European Office Action dated Jan. 9, 2009, corresponding to European Application No. 06 773 243.8-1216.

\* cited by examiner

POLYMER BASED COMPOSITIONS AND CONJUGATES OF NON-STEROIDAL ANTI-INFLAMMATORY DRUGS

CROSS REFERENCE TO RELATED APPLICATIONS

This application claims the benefit of priority to Provisional Application Ser. No. 60/691,846, filed Jun. 17, 2005, which is incorporated herein by reference in its entirety.

FIELD OF THE INVENTION

The present invention relates generally to the delivery of non-steroidal anti-inflammatory drugs (NSAIDs). More particularly, the invention relates to water-soluble polymer conjugates and polymer-based compositions of NSAIDs. In addition, the invention encompasses methods for synthesizing such conjugates and compositions, as well as methods for treating conditions responsive to NSAID therapy by administering the compositions described herein.

BACKGROUND OF THE INVENTION

NSAIDs are an important therapeutic class of drugs typically used to suppress pain and inflammation. Drugs belonging to this class typically possess one or more of the following four major activities: analgesic (provide relief of pain by a mechanism other than reduction of inflammation), antipyretic (ability to lower elevated body temperature), anti-inflammatory (ability to reduce inflammation), and uricosuric (ability to promote excretion of uric acid, e.g., for treating gout); recently, certain NSAIDs have also emerged as effective cancer chemotherapeutic and chemopreventive agents (Mehanna, A. S., *Am. J. of Pharmaceutical Education* 2003: 67(2), Article 63; Koki, A. T., et al., *Expert Opin Investig Drugs*, 1999, 8:1623-38). The mechanism of action of NSAIDs involves reproduction of prostaglandin synthesis by inhibition of the cyclooxygenase (COX) enzyme through competitive antagonism for arachidonic acid binding to COX. Structurally, NSAIDs possess both a lipophilic and an acidic moiety, which enables them to mimic the natural substrate chemistry of COX binding. Structural classes of NSAID compounds include the following: (i) the salicylates (e.g., aspirin belongs to this category), (ii) aniline derivaties (such as acetaminophen), (iii) pyrazole derivatives such as Felsol®, (iv) N-arylanthranilic acid derivatives (also known as fenamates), (v) indole-3-acetic acid derivatives such as Indocin®, (vi) other arylacetic and arylpropionic acid derivatives such as Naprosyn®, Advil®, Toradol® and (vii) oxicams such as Feldene®.

Although these drugs are commonly administered for pain management, their side effects can range from minor to severe. Associated side effects include stomach upset, headache, drowsiness, easy bruising, asthma, high blood pressure and/or fluid retention. The most serious risks associated with NSAID treatment are gastrointestinal, such as the occurrence of gastrointestinal mucosal injury. In severe cases, serious gastrointestinal toxicity, such as bleeding, peptic ulceration, perforation and gastrointestinal bleeding (which can sometimes be severe and occasionally fatal) can occur, with or without warning symptoms, during NSAID therapy. In fact, gastrointestinal side effects cause an estimated 16,000 deaths and 107,000 cases of hospitalization each year in the United States (Fries, J., et al., 1998, *Clinical Significance and Potential of Selective Cox-2 Inhibitors*, William Harvey Press (London), 557-573). In the case of ketorolac, a drug frequently used for relief of moderate to severe post-operative pain, its recommended course of administration is limited to no longer than 5 days, due to the high likelihood of severe gastric-related side-effects associated with longer term administration and/or high doses of this drug. This is unfortunate, since clinical studies have indicated that ketorolac, a non-narcotic analgesic, possesses a single dose efficacy greater than that of morphine for postoperative pain, making it a highly desirable painkiller of choice. Thus, ketorolac, along with other members of the NSAID class of molecules, could benefit from alternative drug forms or delivery systems that are capable of prolonging the course of dosing and/or ameliorating some of the severe side effects associated with its administration.

Although alternative delivery systems have been explored to date, none have proven to be extremely effective in solving the drawbacks associated with administration of NSAIDs such as ketorolac. Such approaches have included passive transdermal delivery, iontophoretic administration, as well as nasal formulations.

For example, in an exploration of the passive transdermal delivery of ketorolac through human skin, the in vitro flux of ketorolac through cadaver skin was found to decrease substantially upon lamination of a pressure sensitive adhesive onto a microporous membrane (Roy, S. D., Manoukian, E., *J. Pharm. Sci.* 1995, 84(10): 1190-6). Iontophoretic-facilitated transdermal transport of ketorolac through rat skin has also been investigated (Tiwari, S., Udupa, *Int. J. Pharmaceutics*, 260 (1), July 2003:930103). While iontophoresis resulted in an improvement of ketorolac drug flux in comparison to diffusion-based transport, the most effective improvement was observed in the case of an extremely cumbersome trimodal regime: pre-treatment with D-limonene in ethanol in combination with ultrasound, followed by iontophoretic-facilitated delivery. In fact, in order to achieve a significant degree of drug transport, the authors had to rely upon both physical (iontophoresis and phonophoresis) and chemical (chemical penetration enhancer) methods. Moreover, both iontophoretic administration and the use of certain chemical penetration enhancers such as d-limonene, are often accompanied by skin irritation and rash—making this administration regime unattractive for widespread patient use. Moreover, complicated administration regimes such as the foregoing are frequently accompanied by extremely low patient compliance. Various types of nasal formulations of ketorolac have also been investigated including spray and powder formulations (Quadir, M. et al., *Drug. Deliv.* 2000 7(4):223-9). Drawbacks associated with such nasal formulations included limited dissolution of ketorolac into the mucous layer, resulting in reduced absorption into the bloodstream, and limited drug release from a polymer-matrix based powder formulation.

Thus, there is a need in the art for improved NSAID compositions, e.g., for localized or non-localized delivery, preferably allowing less frequent patient dosing and a reduced occurrence of severe associated side effects. This invention meets these needs.

SUMMARY OF THE INVENTION

Accordingly, in one aspect, the invention provides improved pharmaceutical compositions of NSAIDs, and in particular, carboxyl-containing NSAIDs such as ketorolac and diclofenac, among others, e.g., for the treatment of pain. The conjugates and compositions of the invention are particularly suited for localized delivery, thereby solving or ameliorating some of the severe gastric-related problems associated with long-term dosing of oral NSAIDs such as ketorolac.

The conjugates and compositions described herein also advantageously reduce immunogenicity. Equally important, the present conjugates and compositions require a decreased frequency of dosing compared to traditional NSAID compositions absent water-soluble polymer, either in conjugated or non-conjugated form. Thus, the conjugates and compositions provided herein advantageously allow a longer course of dosing when compared to their non-conjugated counterparts by virtue of their release properties, which act to provide extended and therapeutic levels of an NSAID, preferably a carboxyl-containing NSAID, at an intended site of action.

In one aspect, the invention is directed to a conjugate of a water-soluble polymer and a NSAID. Exemplary conjugates in accordance with this aspect of the invention are provided in herein.

In a preferred embodiment, the conjugates and compositions of the invention are degradable, that is to say, comprise at least one degradable linkage, preferably a hydrolyzable linkage.

For example, the hydrolyzable linkage in a conjugate or composition of the invention may comprise a hydrolyzable moiety such as a carboxylate ester, a phosphate ester, a carbamate, an anhydride, an acetal, a ketal, an acyloxyalkyl ether, an imine, an orthoester, a thioester, a thiolester, or a carbonate.

In a preferred embodiment, the hydrolyzable moiety comprises an ester or a carbonate bond.

In yet a more particular embodiment, a conjugate of the invention comprises a non-steroidal anti-inflammatory drug (NSAID) having the structure (prior to covalent attachment):

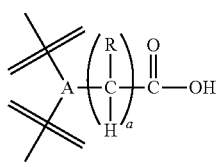

Structure I where

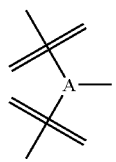

represents a heterocyclic or homocyclic organic ring system that contains at least one aromatic ring component, a is selected from the group consisting of 0, 1, and 2, A is carbon (C) or nitrogen (N), and R, in each occurrence, is independently H or an organic radical that is either alkyl or substituted alkyl, covalently attached to a water-soluble polymer by a degradable linkage.

Water-soluble polymers for use in the invention include but are not limited to poly(alkylene oxide), poly(vinyl pyrrolidone), poly(vinyl alcohol), polyoxazoline, and poly(acryloylmorpholine). Preferably, the water-soluble polymer is a poly(alkylene oxide); more preferably, the water soluble polymer is a poly(ethylene glycol). A water-soluble polymer in accordance with the invention may possess any of a number of architectures or geometries, including linear, branched, forked, and multi-armed.

The water-soluble polymer may terminate in one or more hydroxyl groups, or alternatively, may be terminally capped with an end-capping moiety such as alkoxy, substituted alkoxy, alkenoxy, substituted alkenoxy, alkynoxy, substituted alkynoxy, aryloxy and substituted aryloxy. Preferably, the polymer is terminally capped with an end-capping group that is a methoxy, ethoxy, or benzyloxy. Alternatively, the water-soluble polymer is terminally capped with drug, e.g., NSAID, itself.

Exemplary molecular weight ranges of the water-soluble polymer, e.g., polyethylene glycol, include the following: from about 200 daltons to about 100,000 daltons, from about 500 daltons to about 75,000 daltons, from about 1,000 daltons to about 60,000 daltons, from about 2,000 daltons to about 50,000 daltons, and from about 5,000 daltons to about 45,000 Daltons.

In accordance with yet another embodiment of the invention, the water soluble polymer possesses a molecular weight selected from the group consisting of about: 200 daltons, 300 daltons, 400 daltons, 500 daltons, 750 daltons, 1000 daltons, 1500 daltons, 2500 daltons, 3000 daltons, 5000 daltons, 10,000 daltons, 15,000 daltons, 20,000 daltons, 25,000 daltons, 30,000 daltons, 40,000 daltons, 50,000 daltons, and 60,000 daltons.

In one embodiment, the heterocyclic or homocyclic organic ring system is selected from benzene, indole, indenyl, pyrrolizine, oxazole, and naphthalene, each of which may be substituted or unsubstituted. Particular substituted or unsubstituted benzenes include substituted or unsubstituted: biphenyl, diphenylamine, and diphenyl ether.

In a preferred embodiment, A is C (carbon).

Particular embodiments include those where (i) R in each occurrence is independently H or an organic radical that is either lower alkyl or substituted lower alkyl, (ii) R is selected from the group consisting of H, methyl, ethyl and propyl, and (iii) R is H or methyl.

In yet a further embodiment, the NSAID is selected from the group consisting of ketorolac, ibuprofen, oxaprozin, indomethecin, etodolac, sulindac, diclofenac, flufenamic acid, difunisal, naproxen, flurbiprofen, ketoprofen, and fenoprofen. A preferred NSAID is ketorolac.

Also forming part of the present invention is a conjugate comprising the structure:

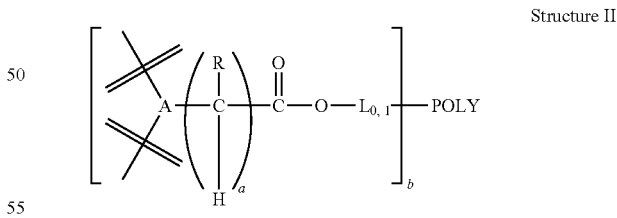

Structure II where POLY is a water-soluble polymer, L is an optional linker interposed between POLY and the carboxyl oxygen, and b is an integer ranging from 1 to about 20.

In yet a further embodiment, b is an integer selected from 1, 2, 3, 4, 5, 6, 7, 8, 9, and 10.

In yet another embodiment, the conjugate is linear and b is 1 or 2.

Alternatively, POLY is linear and b is an integer ranging from 1 to about 20. In such instances when b is greater than 2, the linear polymer possesses pendant NSAID's covalently attached along the polymer chain.

The optional linker, L, when present, is designated in Structure II as "$L_1$" and when absent, is designated in Structure II as $L_0$, where the zero subscript indicates the absence of such linker. In one embodiment of the invention, L possesses a length selected from the the following: from about 1 to about 30 atoms, from about 2 to about 20 atoms, and from about 3 to about 15 atoms.

In reference to Structure II, POLY may be linear, branched or multi-armed. In one embodiment, (i) POLY comprises 2 or more polymer arms, (ii) the number of polymer arms corresponds to the value of b, and (iii) each polymer arm terminates in the structure:

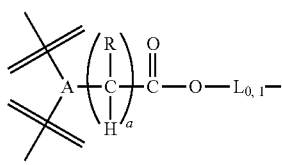

Structure IV

In yet another embodiment, POLY comprises 2 or more polymer arms, one or more of which terminates in Structure IV. In this instance, the value of b is less than or equal to the number of polymer arms, depending upon the degree of conjugation of the product.

In yet another embodiment, POLY is linear and the conjugate is bifunctional, possessing the structure:

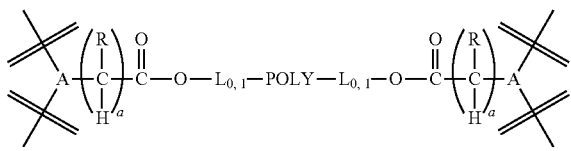

Structure III where each of the variables is independently selected. That is to say, in Structure III, each of

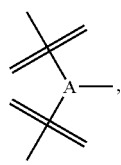

R, a, and L, on either side of POLY is independently selected. In the instance where the terminus on one side of POLY differs from that on the other side, the conjugate is considered to be heterobifunctional. In the instance where the conjugate is symmetrical, i.e., both termini are identical, the conjugate is considered to be homobifunctional. In a preferred embodiment, the NSAID and L are the same on each side of POLY, thereby providing a homobifunctional polymer conjugate having two drug moieties attached at the ends (or termini) of a linear polymer. Such a structure is commonly referred to as possessing a "dumbbell" structure.

According to yet another embodiment, a conjugate of the invention comprises a multi-armed polymer that comprises a central core from which extends three or more independently selected polymer arms. The polymer arms may be homopolymeric or co-polymeric. In one such embodiment of a multi-armed polymer conjugate comprising co-polymeric arms, each polymer arm comprises a copolymer comprising an inner polypeptide segment covalently attached to the central core and an outer hydrophilic polymer segment covalently attached to the polypeptide segment. One such exemplary polymer conjugate possesses the structure below:

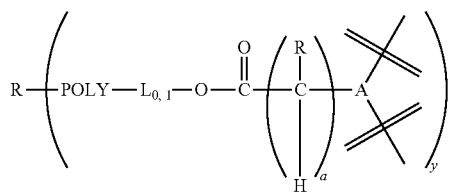

Structure V where R is a core molecule, L and POLY are as previously defined, and y is an integer ranging from 3 to 15, e.g., 3, 4, 5, 6, 7, 8, 9, 10, 11, 12, 13, 14, or 15. For multi-armed embodiments, each polymer arm, including the covalently attached drug, if present, is independently selected, such that the overall multi-armed polymer may comprise arms having different polymers, and/or linkers, and/or NSAIDs. Preferably, each polymer arms is identical.

In yet a more particular embodiment, a conjugate of the invention comprises a structure selected from the group consisting of:

Structure VI

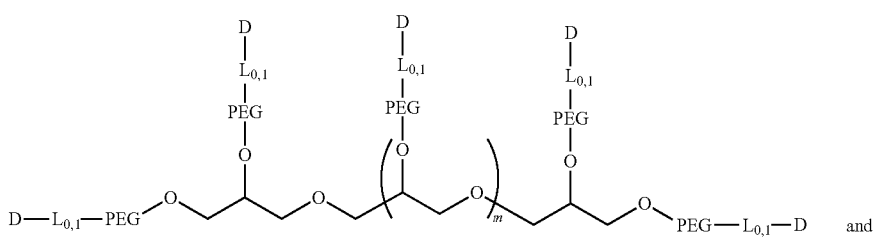

and

-continued

Structure VII

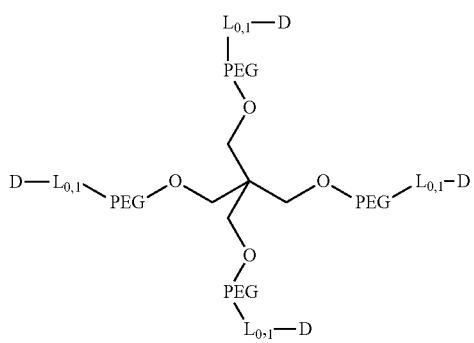

where m is an integer selected from 3, 4, 5, 6, 7, and 8, D is a NSAID having the structure:

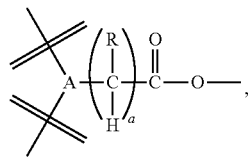

and the remaining variables are as previously defined.

In preferred embodiments of the herein described conjugates and drug delivery systems, the NSAID is ketorolac.

Also forming part of the present invention are pharmaceutical compositions comprising any one or more of the herein described conjugates. The compositions encompass all types of formulations and in particular those that are suited for injection or implantation, e.g., for localized delivery.

In yet another aspect, the invention is directed to a hydrogel comprising an NSAID having the structure:

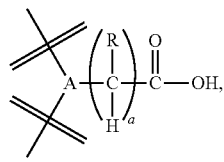

where the variables are as previously described, and as one of the gel components, a polyalkylene oxide. A hydrogel in accordance with the invention may be crosslinked or non-crosslinked, and the NSAID contained therein may be conjugated to a water-soluble polymer or non-conjugated. Preferably, a hydrogel of the invention is degradable under physiological conditions. In one embodiment, the NSAID is optionally covalently attached to one or more gel components via a degradable linkage.

In yet another aspect, the invention is directed to a method of making an NSAID polymer conjugate. The method comprises the step of contacting, under conjugation conditions, an NSAID having a structure as previously defined, with a water soluble polymer reagent effective to form a NSAID covalently attached to the water-soluble polymer by a degradable linkage.

In a further aspect, the invention encompasses a method for preparing a hydrogel comprising an NSAID having a structure as previously described. In the method, suitable hydrogel precursor reagents are contacted with each other and with the NSAID under conditions effective to promote gelling of the precursor reagents, to thereby form a hydrogel comprising the NSAID entrapped therein. The NSAID is either in conjugated or unconjugated form.

In accordance with yet another aspect, the present invention is directed to a method of treating in a mammalian subject a condition responsive to NSAID treatment, where the method comprises administering a composition comprising a therapeutically effective amount of any one or more of the herein described conjugates or NSAID-containing delivery systems in combination with a pharmaceutically acceptable excipient. Typically, the step of administering is by injection (e.g., intramuscular injection, intravenous injection, subcutaneous injection, and so forth), although alternative modes of administration are contemplated (e.g., oral, implant, infusion pump, transdermal, nasal, etc.).

In yet a further aspect, the invention is directed to a method of extending the half-life of a NSAID. In the method, an NSAID (having a structure as previously described) is contacted, under conjugation conditions, with a water-soluble polymer reagent to form a NSAID covalently attached to the water-soluble polymer by a degradable linkage. The method thereby provides a conjugate that exhibits a half-life that is extended at least 2 fold over that of the corresponding non-conjugated NSAID when measured in vitro at 37° C. in phosphate buffered saline. Preferably, the half-life is extended at least ten times over that of the corresponding non-conjugated NSAID, and even more preferably, is extended at least 20 times over that of the corresponding non-conjugated NSAID.

In yet another aspect, the present invention is directed to a method of reducing pain or inflammation in a mammalian subject. Such method comprises administering a composition comprising a therapeutically effective amount of an NSAID-based conjugate or delivery system as described herein, in combination with a pharmaceutically acceptable excipient. In one embodiment, a composition or delivery system as previously described is administered locally, e.g., at an incision site or the like, in an amount effective to reduce pain or inflammation.

Each of the herein-described features of the invention is meant to apply equally to each and every embodiment as described herein, unless otherwise indicated.

Additional objects, advantages and features of the invention will be set forth in the description that follows, and in part, will become apparent to those skilled in the art upon reading the following, or may be learned by practice of the invention.

DETAILED DESCRIPTION OF THE INVENTION

Definitions

Figure 1:
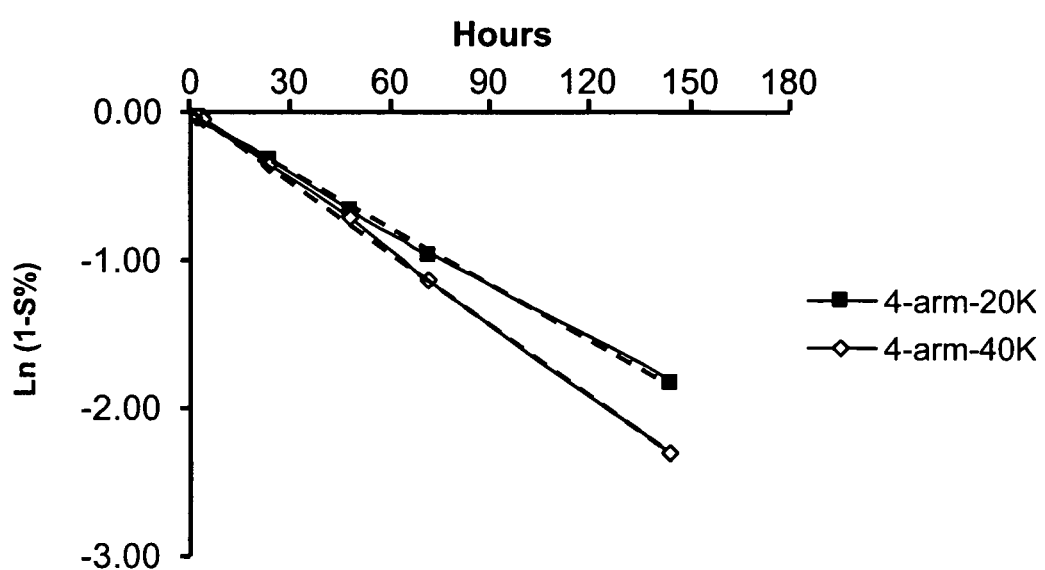
FIG. 1. is a plot demonstrating the kinetics of the in vitro release of ketorolac from two exemplary 4-arm PEG-based delivery systems (40 kDa and 20 kDa) in phosphate buffered saline at 37° C. as described in detail in Example 3.

Before describing the present invention in detail, it is to be understood that this invention is not limited to the particular polymers, hydrogels, synthetic techniques, NSAIDs, and the like, explicitly described herein, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to a "an optional excipient" refers to a single optional excipient as well as two or more of the same or different optional excipients, and the like.

In describing and claiming the present invention, the following terminology will be used in accordance with the definitions described below.

"PEG," "polyethylene glycol" and "poly(ethylene glycol)" as used herein, are interchangeable and meant to encompass any water-soluble poly(ethylene oxide). Typically, PEGs for use in accordance with the invention comprise the following structure "—$(OCH_2CH_2)_n$—" where (n) ranges from 2 to about 4000. As used herein, the term "PEG" may also refer to the particular structures "—$CH_2CH_2$—O—$(CH_2CH_2O)_n$—$CH_2CH_2$—" or "—$(OCH_2CH_2)_nO$—," depending upon whether or not the terminal oxygens have been displaced; the particular PEG structure referred to will be obvious in view of the context in which it is used. Throughout the specification and claims, it should be remembered that the term "PEG" includes structures having various terminal or "end capping" groups and so forth. The term "PEG" refers to a polymer that contains a majority, that is to say, greater than 50%, of —$OCH_2CH_2$— repeating subunits. Preferably, "PEG" refers to a polymer that contains at least 60%, or at least 70%, or at least 80%, or at least 90% or at least 95%, or 100% of repeat units that are —$OCH_2CH_2$—. Preferably, "PEG" refers to a polyethylene glycol polymer segment that contains only (—$OCH_2CH_2$) monomer subunits. With respect to specific forms, the PEG can take any number of a variety of molecular weights, as well as structures or geometries, such as "branched," "linear," "forked," "multifunctional," and the like, to be described in greater detail below.

The terms "end-capped" and "terminally capped" are used interchangeably herein to refer to a terminus of a polymer having an end-capping moiety. Typically, although not necessarily, the end-capping moiety comprises a hydroxy or $C_{1-20}$ alkoxy group or benzyloxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It should be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the label and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes) labels, metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water-soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight, in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity (PDI) values of preferably less than about 1.2, more preferably less than about 1.15, still more preferably less than about 1.10, yet still more preferably less than about 1.05, and most preferably less than about 1.03. Polymers (or more properly, ethylene glycol oligomers) having a small number of subunits, e.g., from 2 to about 50 or so, may have a polydispersity as indicated above, or may be monodisperse, i.e., where each polymer in a given composition has the same number of subunits, such that the ratio of the number average molecular weight to the weight average molecular weight is equal to 1.

By overall atom length, e.g., in the context of a linker (L) of the invention, is meant the number of atoms in a single chain, not counting substituents. For instance, —CH$_2$-counts as one atom with respect to overall linker length, —CH$_2$CH$_2$O— counts as 3 atoms in length, and a non-linear group such as a phenyl ring counts as 4 atoms in length.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "linkage" or "linker" are used herein to refer to an atom or a collection of atoms optionally used to link interconnecting moieties such as a terminus of a polymer segment and an NSAID (e.g., ketorolac). A linker may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably C$_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, C$_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucelophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides. In certain embodiments of the invention, preferred are bonds that have a hydrolysis half-life at pH 8, 25° C. of less than about 30 minutes, although such preference is not intended to be limiting in any sense.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. For example, a hydrolytically stable linkage is typically but not necessarily one that exhibits a rate of hydrolysis of less than about 1-2% per day under physiological conditions. Hydrolysis rates of representative chemical bonds can be found in most standard chemistry textbooks.

"Conjugation conditions" refers to reaction conditions effective to result in covalent attachment of a given water soluble polymer to one or more particular active agents, such as an NSAID. Conditions for covalently attaching a polymer to an active agent are known or can be readily determined by those skilled in the area of polymer chemistry, conjugation chemistry, and the like. See, for example, Veronese, F. M., Morpurgo, M., "*Bioconjugation in Pharmaceutical Chemistry*", in *Il Farmaco*, 54 (8), 30 Aug. 1999, 497-516; Wong, S. S., Ed. "*Chemistry of Protein Conjugation and Cross-Linking*", CRC Press, Boca Raton, Fla., 1991; and Harris, J. M., Ed., *Topics in Applied Chemistry, "Poly(Ethylene Glycol) Chemistry Biotechnical and Biomedical Applications*", Plenum Press, NY, 1992.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a NSAID conjugate or composition (e.g., a hydrogel) that is needed to provide a desired level of the conjugate (or corresponding unconjugated NSAID) in the bloodstream. The precise amount will depend upon numerous factors, e.g., the particular NSAID, the components and physical characteristics of the therapeutic composition, intended patient population, individual patient considerations, and the like, and can readily be determined by one skilled in the art, based upon the information provided herein.

"Branched", in reference to the geometry or overall structure of a polymer, refers to a polymer having two or more polymer "arms" extending from a branch point. A branched polymer may possess, for example, 2 polymer arms, 3 polymer arms, 4 polymer arms, 6 polymer arms, 8 polymer arms or more. A subset of branched polymers are multi-armed polymers, that is to say, polymers having 3 or more arms extending from a central core.

A "branch point" refers to a bifurcation point comprising one or more atoms at which a polymer or linking group splits or branches from a linear structure into one or more additional polymer arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

A functional group in "protected form" refers to a functional group bearing a protecting group. As used herein, the term "functional group" or any synonym thereof is meant to encompass protected forms thereof. Representative protecting groups are described in, Greene, T., Wuts, P. G., "*Protective Groups in Organic Synthesis*", 3$^{rd}$ Ed., John Wiley & Sons, Inc., 1999.

"Multi-functional" means a polymer having 3 or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "hydrogel" is a material that absorbs a solvent (e.g. water), undergoes rapid swelling without discernible dissolution, and maintains three-dimensional networks capable of reversible deformation. Hydrogels may be uncrosslinked or crosslinked. Covalently (chemically) crosslinked networks of hydrophilic polymers, such as PEG, can form hydrogels (or aquagels) in the hydrated state. Uncrosslinked hydrogels are typically block copolymers having hydrophilic and hydrophobic regions. These uncrosslinked materials can form hydrogels when placed in an aqueous environment, due to physical crosslinking forces resulting from ionic attractions, hydrogen bonding, Van der Waals forces, etc. They are able to absorb water but do not dissolve due to the presence of hydrophobic and hydrophilic regions.

"Substantially" or "essentially" means nearly totally or completely, for instance, 95% or greater of some given quantity.

The terms "subject", "individual" or "patient" are used interchangeably herein and refer to a vertebrate, preferably a mammal, suffering from or prone to a condition that can be prevented or treated by administration of an active agent of the invention (e.g., conjugate). The term "subject" includes both humans and animals. Mammals include, but are not limited to, murines, rodents, simians, humans, farm animals, sport animals and pets.

"Optional" or "optionally" means that the subsequently described circumstance may or may not occur, so that the description includes instances where the circumstance occurs and instances where it does not.

Overview: Polymer Compositions of NSAIDs

As stated previously, the present invention provides compositions and methods for sustained delivery of NSAIDs such as ketorolac, ibuprofen, oxaprozin, indomethecin, etodolac, sulindac, diclofenac, flufenamic acid, difunisal, naproxen, flurbiprofen, ketoprofen, and fenoprofen, among others. Described herein are polymers, conjugates and compositions for prolonging the half-life of short-acting NSAIDs, particularly those comprising a carboxyl group, whilst also maintaining at least a measurable, and more preferably, a significant degree of their activity upon administration. In certain instances, preferred are polymer conjugates having one or more hydrolyzable linkages designed to release the polymer portion of the conjugate in vivo, thereby releasing the parent NSAID in its original form, or degradable hydrogel-based compositions, to be described in greater detail herein. In particular, for drugs such as the NSAIDs described herein, conjugates possessing one or more degradable linkages possess the advantages of having a prolonged half-life, and maintaining bioactivity in vivo by virtue of the degradable nature of the polymer attachment, since the polymer is released from the NSAID upon hydrolysis. Thus, in such embodiments, the impact of the size and position of polymer attachment on the activity of the resultant conjugate is not of particular concern, since the polymer portion of the molecule falls off in the body to release the NSAID in its original form.

Non-Steroidal Anti-Inflammatory Drug

The conjugates and compositions of the invention comprise at least one carboxyl-containing NSAID. NSAIDs possess both analgesic and antipyretic properties, and are used therapeutically to suppress pain and inflammation. Additionally, certain NSAIDs have been used as cancer chemotherapeutic and chemopreventative agents. The mechanism of action of NSAIDs involves reproduction of prostaglandin synthesis by inhibition of COX enzyme through competitive antagonism for arachidonic acid binding to the cyclooxygenase enzyme (COX). NSAIDs possess both lipophilic and acidic properties, which enables them to mimic the natural substrate chemistry. As described previously, in general, unmodified NSAIDs exhibit adverse effects on the gastrointestinal tract, with the most severe and detrimental effect, associated with prolonged use, being the development of gastric ulceration.

Preferred NSAIDs in accordance with the invention are those typically falling within one of the following chemical classifications: indole-3-acetic acid derivatives, arylalkanoic acid derivatives, anthranilic acid derivatives, and indole analogs. NSAIDs for use in the invention typically contain at least one aromatic ring component such as a pyrrolizine, benzene, oxazole, indole, indenyl, 1,3,4,4a,9,9a-hexahydropyrano[3,4-b]indole, biphenyl, diphenylamine, diphenyl, naphthalene, diphenylmethanone or diphenylether.

More particularly, a NSAID for use in the conjugates and delivery systems of the invention is generally characterized by the following structure:

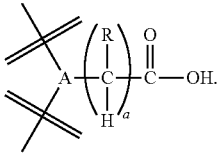

Structure I where

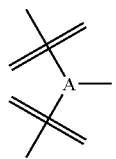

represents a heterocyclic or homocyclic organic ring system that contains at least one aromatic ring component, a is selected from the group consisting of 0, 1, and 2, A is carbon (C) or nitrogen (N), and R in each occurrence, is independently H or an organic radical that is either alkyl or substituted alkyl. Preferably, R, in each occurrence is H or lower alkyl such as methyl or ethyl.

Illustrative heterocyclic or homocyclic organic rings systems include the following, where for each ring system below (e.g., Structures IX-XX), a is selected from the group consisting of 0, 1, and 2, R in each occurrence is independently H or an organic radical that is either alkyl or substituted alkyl. Preferably, R in each occurrence is H or lower alkyl such as methyl or ethyl.

TABLE 1

Representative Heterocyclic Ring Systems,

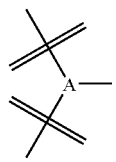

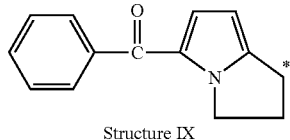

Structure IX

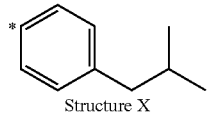

Structure X

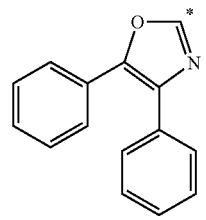 [SMILES: c1ccc(-c2ncoc2-c2ccccc2)cc1]

Structure XI

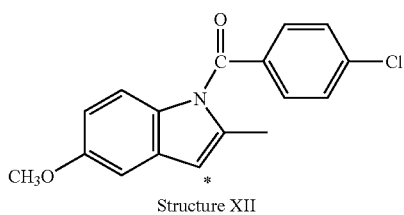

Structure XII

TABLE 1-continued

Representative Heterocyclic Ring Systems,

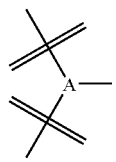

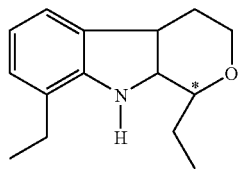 [SMILES: CCc1cccc2c1NC1C(CC)OCCC21]

Structure XIII

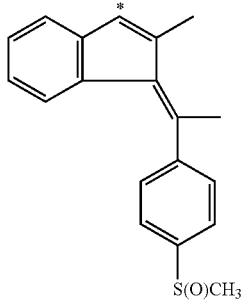

Structure XIV

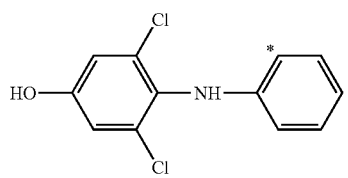 [SMILES: Oc1cc(Cl)c(Nc2ccccc2)c(Cl)c1]

Structure XV

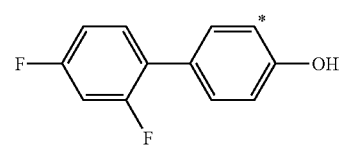

Stucture XVI

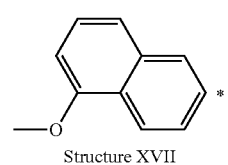

Structure XVII

TABLE 1-continued

Representative Heterocyclic Ring Systems,

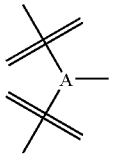

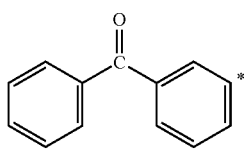

Structure XVIII

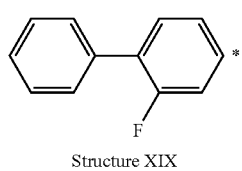

Structure XIX

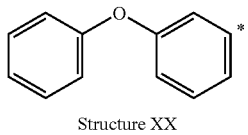

Structure XX

TABLE 1-continued

Representative Heterocyclic Ring Systems,

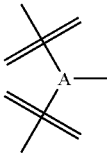

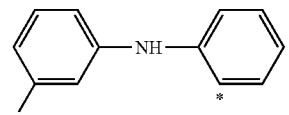

Structure XXI

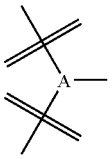

* indicates the point of attachment to

A is equal to C in each of the above structures.

Particularly preferred NSAIDs for use in the invention include ketorolac (Toradol®), ibuprofen (Motrin®), oxaprozin (Daypro®), indomethecin (Indocin®), etodolac (Lodine®), sulindac (Clinoril®), diclofenac (Voltaren®), flufenamic acid, difunisal (Dolobid®), naproxen (Aleve®, Naprosyn®), flurbiprofen (Ansaid®), ketoprofen (Orudis®), and fenoprofen (Nalfon®), where the corresponding brand names (not necessary inclusive) are indicated in parentheses. For preferred NSAIDs, values for the heterocyclic or homocyclic organic ring system, R, and a, are provided below. Also provided are the chemical structures of preferred NSAIDs themselves, prior to modification with a water-soluble polymer in accordance with the invention.

TABLE 2

Illustrative NSAIDs

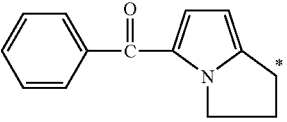

| | R | a | Drug |
|---|---|---|---|
| 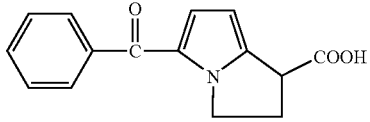 Structure IX | — | 0 | 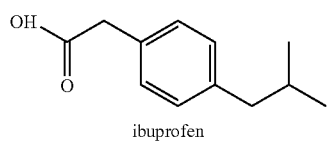 ketorolac |
| 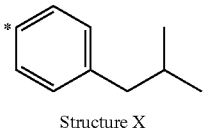 Structure X | —CH₃ | 1 | ibuprofen |

TABLE 2-continued

Illustrative NSAIDs

| | R | a | Drug |
|---|---|---|---|
| Structure XI | H(both) | 2 | oxaprozin |
| Structure XII | H | 1 | indomethacin |
| Structure XIII | H | 1 | etodolac |
| Structure XIV | — | 0 | sulindac |

TABLE 2-continued

Illustrative NSAIDs

| | R | a | Drug |
|---|---|---|---|
| Structure XV | H | 1 | diclofenac |
| Structure XVI | — | 0 | difunisal |
| Structure XVII | —CH₃ | 1 | naproxen |
| Structure XVIII | —CH₃ | 1 | Ketoprofen |
| Structure XIX | —CH₃ | 1 | flurbiprofen |
| Structure XX | —CH₃ | 1 | fenoprofen |
| Structure XXI | — | 0 | flufenamic acid |

As can be seen from looking at the structures herein, the NSAID per se, prior to covalent attachment to a water soluble polymer, contains a carboxylic acid function, which, in a resulting polymer conjugate, is typically converted to its corresponding residue, —C(O)—O—. This ester function, when present in a conjugate, is hydrolyzable, lending to the conjugates and delivery systems herein a prodrug feature, such that upon hydrolysis in vivo, the unmodified parent drug is released.

Many of the herein described NSAIDs contain at least one chiral center. This means that a compound for use in the present invention can by used as a racemate (a racemic mixture of enantiomers), or in chiral form. Mixtures of enantiomers may also be employed, in any relative amounts. In general, the S(+) isomer of any given NSAID is the active form, while the R(−) isomer is inactive. Fortunately, the R(−) isomer of most NSAIDs is converted to the corresponding S(+) isomer in vivo, so that the stereochemistry is typically of little concern, particularly in the case of the prodrugs of the present invention—where the polymer portion falls off in vivo to yield the parent NSAID. Thus, covalent attachment of a water soluble polymer to a racemate or an inactive form of an NSAID does not present a significant concern with respect to the bioactivity of the resulting conjugate, since any conversion of the NSAID in vivo to its active isomer should proceed in its normal fashion once the polymer portion is hydrolysed in vivo. Certain NSAIDs such as ibuprofen and ketoprofen are typically administered as racemates, while naproxen, in its unmodified form, is marketed both as its S(+) isomer (Naprosyn®) and as its R(−) isomer (Anaprox®).

In another aspect of the invention directed to a conjugate wherein the covalent attachment linking the NSAID to the water-soluble polymer is not degradable, preferred in one embodiment is a low molecular weight polymer (e.g., possessing a molecular weight of about 100 daltons to about 5000 daltons, or from about 2 to about 115 monomer subunits) for covalent attachment to an NSAID, such that bioactivity of the NSAID is unlikely to be adversely affected. Preferred molecular weight ranges are selected from the following: from about 100 to about 5000 daltons, from about 100 to about 3000 daltons, from about 100 to about 2200 daltons, from about 100 to 1500 daltons, from about 100 to about 1000 daltons, and from about 100 to about 750 daltons. More preferred polymer molecular weights for this aspect of the invention, i.e., one in which the polymer is attached to the NSAID via a stable, non-hydrolyzable linkage, are selected from the group consisting of about 100, 150, 175, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1750, 2000, 2500, 3000, 3500, 4000, 4500, and 5000 daltons. In other words, a particularly preferred polymer in accordance with this aspect of the invention possesses a number of monomers selected from the group consisting of 2-100, 2-50, 2-40, 2-30, 2-20, and 2-10 subunits. More particularly, the polymer possesses a number of monomers selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50.

NSAIDs for use in the invention are obtainable from commercially-available sources.

Polymers

As previously discussed, one aspect of the invention is directed to a conjugate of an NSAID, such as ketorolac or naproxen or the like (as described above) attached to a water-soluble polymer, often designated herein simply as POLY. With respect to the water-soluble polymer, the water-soluble polymer is nonpeptidic, nontoxic, non-naturally occurring and biocompatible. A substance is generally considered biocompatible if the beneficial effects associated with use of the substance alone or with another substance (e.g., active agent such an entry inhibitor) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer of the invention is both biocompatible and nonimmunogenic.

Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing. A polymer of the invention may be a homopolymer, alternating copolymer, random copolymer, block copolymer, alternating tripolymer, random tripolymer, or a block tripolymer made up of monomers of any of the preceding polymers. Preferably, the polymer is a copolymer, or, more preferably, is a homopolymer, e.g., of polyethylene glycol. Although much of the discussion herein is focused upon PEG as an illustrative water-soluble polymer, the discussion and structures presented herein are meant to encompass any of the water-soluble polymers described above. More specifically, for exemplary structures and figures demonstrating "PEG" as the water-soluble polymer, the term "PEG" is also meant to be substituted with any of the alternative water-soluble polymers described herein, such that the structures and figures provided herein explicitly extend to such alternative water-soluble polymers.

The polymer per se, prior to conjugation to a NSAID, is typically characterized as having from 2 to about 300 termini, more preferably from about 2 to about 25 termini, even more preferably having 2, 3, 4, 5, 6, 7, 8, 9, or 10 termini.

The polymer is not limited to a particular structure and can be linear (e.g., end-capped PEG or linear bifunctional PEG), branched or multi-armed. Typically, PEG and other water-soluble polymers, prior to conjugation with a NSAID, are activated with a suitable activating group appropriate for coupling to a desired site on the drug. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), in Zalipsky (1995) Advanced Drug Reviews 16:157-182, in Roberts, M. et al., "*Chemistry for Peptide and Protein PEGylation*", Advanced Drug Delivery Reviews 54 (2002): 459-476, and in "*Nektar Advanced PEGylation: Polyethylene Glycol and Derivatives for Advanced PEGylation,*" Catalogs 2004, and 2005-2006.

Typically, the weight average molecular weight of the non-peptidic water-soluble polymer in the conjugate is from about 100 Daltons to about 150,000 Daltons. Exemplary ranges, however, include weight-average molecular weights in the range of about 500 Daltons to about 100,000 Daltons, in the range of about 2,000 Daltons to about 90,000 Daltons, in the range of about 5,000 Daltons to about 85,000 Daltons, in the range of about 10,000 Daltons to about 50,000 Daltons, or in the range of about 15,000 Daltons to about 40,000 Daltons.

Higher molecular weight polymers, e.g., having a molecular weight greater of about 20,000 Daltons or more, or 30,000 Daltons or more, or even 40,000 Daltons or more, or even 50,000 Daltons or more, are preferred in the present instance when covalently attached to a NSAID by means of a hydrolyzable linkage. In one embodiment, use of a high molecular weight and/or branched degradable polymer is preferred, since due to structural constraints on the parent NSAID, it may be possible to covalently attach only one or two molecules of high molecular weight polymer to the NSAID. In this way, formation of a hydrolyzable, mono-polymer conjugate (i.e., having only one polymer molecule covalently attached to the NSAID) or di-polymer conjugate, is favored. This can advantageously lead to a higher yields, along with a cleaner conjugate synthesis and subsequent separation, purification, and characterization, due to the lack of formation of multiple conjugate species. Moreover, when considering the action of the conjugate in vivo, hydrolysis of a mono-polymer conjugate may be particularly advantageous, since only a single hydrolysis reaction is involved, i.e., a hydrolysis effective to release the NSAID and the polymer, in contrast to the degradable, covalent attachment of a polymer to multiple reactive sites upon the NSAID, or, alternatively, multiple NSAID drugs covalently attached to a multi-armed polymer, where release of the polymer or of the drug is complicated by the kinetics involved in multiple hydrolysis steps and intermediate species. Although the use of a degradable, larger molecular weight polymer may, in certain instances, offer certain advantages over alternative conjugate structures or architectures, that is not to say that alternative embodiments, such as the use of smaller polymers, either singly or multiply attached to an NSAID if possible, or other additional embodiments as described herein, are without their own associated advantages, to be described in greater detail below.

Exemplary weight average molecular weights for the water-soluble polymer segment include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched or other multi-arm versions of the water-soluble polymer (e.g., a branched 40,000 Dalton water-soluble polymer having two 20,000 Dalton polymer 'arms') having a total molecular weight of any of the foregoing can also be used.

In instances in which the polymer is PEG, the PEG will typically comprise a number of ($OCH_2CH_2$) monomers. As used throughout the description, the number of repeat units is identified by the subscript "n" in "$(OCH_2CH_2)_n$." Thus, the value of (n) typically falls within one or more of the following ranges: from 2 to about 3400, from about 100 to about 2,300, from about 100 to about 2,270, from about 136 to about 2,050, from about 225 to about 1,930, from about 450 to about 1,930, from about 1,200 to about 1,930, from about 568 to about 2727, from about 660 to about 2730, from about 795 to about 2730, from about 909 to about 2730, and from about 1,200 to about 1,900. For any given polymer in which the molecular weight is known, it is possible to determine the number of repeat units (i.e., "n") by dividing the total molecular weight of the polymer by the molecular weight of the repeat unit. In one embodiment of the invention, the water soluble polymer preferably lacks or is absent a nitric oxide moiety (i.e., a moiety containing an —$NO_2$ group) or a nitric oxide donor such as a S-nitrosothiol, nitrate, nitrite, N-oxo-N-nitrosoamine, and the like. In a more specific embodiment, the water-soluble polymer absent a nitric oxide moiety is a polyethylene glycol.

One particularly preferred polymer for use in the invention is an end-capped polymer, that is, a polymer having at least one terminus capped with a relatively inert group, such as a lower $C_{1-6}$ alkoxy group or a benzyloxy group, although a hydroxyl group can also be used. When the polymer is PEG, for example, it is preferred in many instances to use a methoxy-PEG (commonly referred to as mPEG), which is a form of PEG, typically linear, wherein one terminus of the polymer is a methoxy (—$OCH_3$) group, while the other terminus is a hydroxyl or other functional group that can be optionally chemically modified.

The structure of an mPEG comprises "$CH_3O$—$(CH_2CH_2O)_n$—$CH_2CH_2$—", where the value of (n) is as described above.

Generally speaking, in one aspect, a conjugate of the invention possesses the following structure,

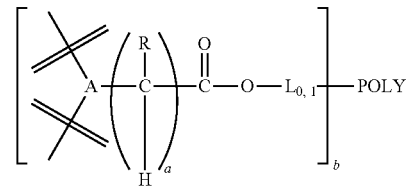

Structure II where L is an optional linker interposed between POLY and the carboxyl oxygen, and b is an integer ranging from 1 to about 20. Structure II encompasses conjugates possessing from one to multiple, e.g., 20, NSAID moieties covalently attached to the polymer segment. The overall conjugate structure can be linear, branched, or multi-armed.

For the sake of simplicity, the NSAID portion of many of the following structures is abbreviated as "NSAID-C(O)—O—", where the —C(O)O-(carboxyl) group, although explicitly shown, is meant to represent the carboxyl moiety of a carboxyl-containing NSAID, and the "NSAID" portion corresponds to

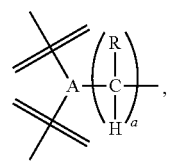

having the variables and structure designations previously described.

Linear polymers, rather than being end-capped, may possess a dumbbell-like or bifunctional linear structure, such that the resulting conjugate is one in which the NSAIDs are interconnected by a central linear POLY such as PEG. More specifically, in one embodiment, such a conjugate is represented by the structure NSAID$_1$-C(O)—O-PEG-O—C(O)—NSAID$_2$, where NSAID$_1$ and NSAID$_2$ are the same or are different, and the conjugate optionally possesses a linker interposed between the carboxyl oxygen (C(O)—O—) and the polymer. Each independent NSAID is selected from the group consisting of: ketorolac, ibuprofen, oxaprozin, indomethecin, etodolac, sulindac, diclofenac, flufenamic acid, difunisal, naproxen, flurbiprofen, ketoprofen, and fenoprofen. Preferably, a conjugate of the invention is one where the polymer, POLY, is covalently attached to ketorolac. In situations in which combination therapy is advantageous, conjugates comprising two different NSAIDs such as those described herein covalently attached to a polymer represent a preferred embodiment. Alternatively, another preferred embodiment is one in which a NSAID along with another type of pharmacogically active agent are covalently attached to a polymer. For example, illustrative combinations include a NSAID and a proton pump inhibitor such as omeprazole (Prilosec®) covalently attached to a polymer. Proton pump inhibitors are effective in reducing the gastric irritation often association with administration of NSAIDs. Further combinations include a NSAID and sumitriptan (useful in the treatment of migraines); a NSAID and a weak opioid (useful in the treatment of cancer-associated pain); and a NSAID and a synthetic prostaglandin E1 analogue such as misoprostol (useful in reducing gastric irritation). Additional combinations include an NSAID and a sympathomimetic agent such as epinephrine; or a NSAID and a corticosteroid such as dexamethasone. The use of such combinations applies equally to the various other embodiments of NSAID conjugates and delivery systems described herein. In an alternative embodiment, an NSAID conjugate as described herein is administered in combination with any one or more of the above described pharmacologically active agents, where such pharmacologically active agent is non-conjugated. Such active agent may be administered simultaneously, sequentially in any order, or separately from the NSAID conjugate.

Thus, exemplary embodiments in accordance with this aspect of the invention include a dumbbell polymer structure having two different NSAIDs attached to opposite termini as described above, or an NSAID and a non-NSAID drug attached at opposite polymer termini, as illustrated by the generalized structure: NSAID-C(O)—O-L$_{0,1}$-POLY-L$_{0,1}$-O—C(O)-Drug, or in a particular embodiment, NSAID-C(O)—O-L$_{0,1}$-PEG-L$_{0,1}$-O—C(O)-Drug. In yet a further embodiment, the linear bifunctional conjugate possesses the structure, NSAID-C(O)—O-L$_{0,1}$-POLY-A, where A in its broadest sense represents a functional group and is different from the NSAID. A, in this regard, may be a functional group suitable for attachment to another moiety, or may be a functional group forming part of a larger molecular structure, such as a label, a drug molecule, a spacer, or the like.

Turning now to embodiments of the invention in which the overall polymer segment is non-linear, a non-linear polymer for use in the invention possesses 2 arms, 3 arms, 4 arms, 5 arms, 6 arms, 7 arms, 8 arms or more. Multi-armed polymers can be used to form conjugates, or alternatively, can be used to form hydrogels, and may possess anywhere from 2 to 300 or so reactive termini.

In one embodiment of the invention, preferred are branched polymer segments having 2 or 3 polymer arms. An illustrative branched POLY, as described in U.S. Pat. No. 5,932,462, corresponds to the structure:

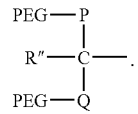

In this representation, R" is a nonreactive moiety, such as H, methyl or a PEG, and P and Q are nonreactive linkages. In the above particular branched configuration, the branched polymer segment possesses a single reactive site extending from the "C" branch point for positioning of the NSAID, optionally via a linker, which may also include a degradable linkage.

In an illustrative embodiment, the branched PEG polymer segment is methoxy poly(ethylene glycol) disubstituted lysine with a single attachment site for covalent attachment to a NSAID. The reactive ester group of the disubstituted lysine may be further modified or activated to form a functional group suitable for reaction with a target group, e.g., carboxyl group, on the NSAID.

Certain branched PEGs having the above-described generalized structure for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts. One particular type of branched PEG-NSAID conjugate corresponds to the structure: (MeO-PEG-)$_i$G-, where i equals 2 or 3, and G is a lysine or other suitable amino acid residue, with a site suitable for attachment to a NSAID as described herein.

Additional branched PEGs for use in the present invention include those described in International Patent Application Publication No. WO 2005/000360 (also U.S. Patent Application No. 2005/0009988). For instance, an additional branched polymer for preparing a NSAID conjugate possesses the structure below,

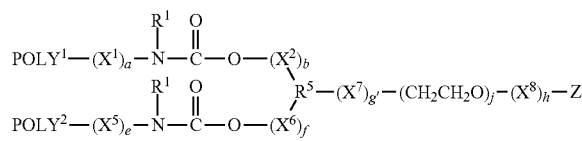

where POLY$^1$ is a water-soluble polymer; POLY$^2$ is a water-soluble polymer; (a) is 0, 1, 2 or 3; (b) is 0, 1, 2 or 3; (e) is 0, 1, 2 or 3; (f) is 0, 1, 2 or 3; (g) is 0, 1, 2 or 3; (h) is 0, 1, 2 or 3; (j) is 0 to 20; each R$^1$ is independently H or an organic radical selected from the group consisting of alkyl, substituted alkyl, alkenyl, substituted alkenyl, alkynyl, substituted alkynyl, aryl and substituted aryl; X$^1$, when present, is a first spacer moiety; X$^2$, when present, is a second spacer moiety; X$^5$, when present, is a fifth spacer moiety; X$^6$, when present, is a sixth spacer moiety; X$^7$, when present, is a seventh spacer moiety; X$^8$, when present, is an eigth spacer moiety; R$^5$ is a branching moiety; and Z is a reactive group for coupling to a NSAID, optionally via an intervening spacer. Preferably, POLY$^1$ and POLY$^2$ in the preceding branched polymer structure are identical, i.e., are of the same polymer type (structure) and molecular weight.

A representative branched polymer falling into the above classification, suitable for use in the present invention is:

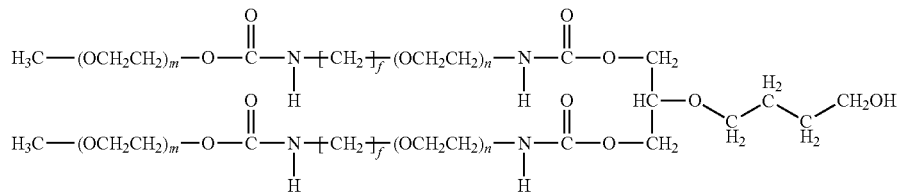

where (m) is 2 to 4000, and (f) is 0 to 6 and (n) is 0 to 20. Alternatively, the —CH$_2$OH terminus can be replaced with —C(O)OH to provide a hydrolyzable anhydride linked conjugate.

Branched polymers useful in preparing a conjugate or hydrogel of the invention additionally include those represented more generally by the formula R(POLY)$_y$, where R is a central or core molecule from which extends 2 or more POLY arms such as PEG. The variable y represents the number of POLY arms, where each of the polymer arms can independently be end-capped or alternatively, possess a reactive functional group at its terminus. A more explicit structure in accordance with this embodiment of the invention possesses the structure, R(POLY-Z)$_y$, where each Z is independently an end-capping group, or a reactive group, e.g., suitable for reaction with a cross-linker or with a NSAID. In yet a further embodiment when Z is a reactive group, upon reaction with, e.g, either a cross-linker or a NSAID, the resulting linkage can be hydrolytically stable, or preferably, is degradable, i.e., hydrolyzable. Typically, at least one polymer arm possesses a terminal functional group suitable for reaction with a NSAID. Branched PEGs such as those represented generally by the formula, R(PEG)$_y$, above possess 2 polymer arms to about 300 polymer arms (i.e., y ranges from 2 to about 300). Preferably, such branched PEGs possess from 2 to about 25 polymer arms, more preferably from 2 to about 20 polymer arms, and even more preferably from 2 to about 15 polymer, or from 3 to about 15 polymer arms or fewer. Most preferred are multi-armed polymers having 3, 4, 5, 6, 7 or 8 arms.

Preferred core molecules in branched PEGs as described above are polyols, which are then typically further derivatized to provide a branched polymer, e.g., by attachment of polymer arms to the core. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm structure corresponding to a multi-armed polymer conjugate of the invention is shown below, where y preferably ranges from about 3 to about 8, R is as defined above, and L is an optional linker that covalently attaches each polymer arm to the carboxyl group of the NSAID. When such a linker is present, its presence is indicated by L$_1$, whereas the absence of such a linker is indicated by L$_0$. As will be described in more detail in the linker section below, although any of a number of linkages can be used to covalently attach a polymer or polymer arm to a NSAID, in certain instances, the linkage may contain at least one bond or moiety that hydrolyzes under physiological conditions, e.g., an ester, hydrolyzable carbamate, carbonate, or other such group.

Structure V

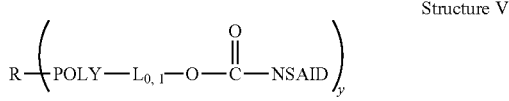

Additional multi-arm polymers useful for forming a multi-arm NSAID-conjugate or hydrogel of the invention include multi-arm PEGs available from Nektar (Huntsville, Ala.). Preferred multi-armed activated polymers for use in the method of the invention correspond to the following structure, where E represents a reactive group suitable for coupling to a NSAID. In one embodiment, E is preferably an —OH, for reaction with a NSAID carboxy group or equivalent.

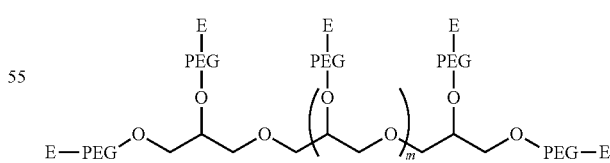

PEG is —(CH$_2$CH$_2$O)$_n$CH$_2$CH$_2$—, and m is selected from the group consisting of 3, 4, 5, 6, 7, and 8. Of course, the corresponding NSAID polymer conjugate product possesses the structure shown above with the exception that the reactive group, E, is replaced by "-L$_{0,1}$-O—C(O)—NSAID as shown below.

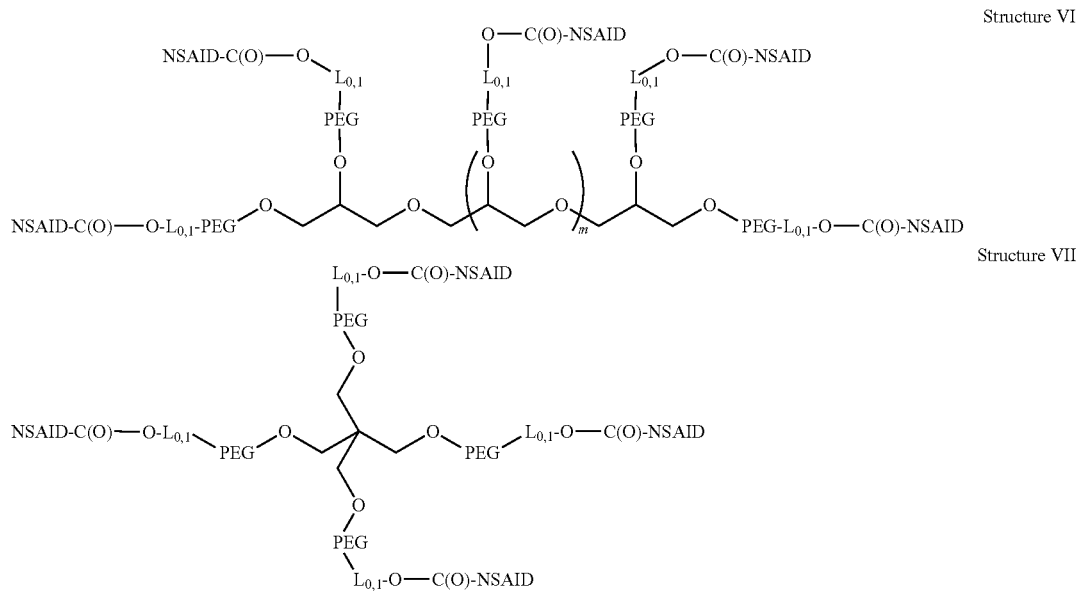

Structure VI

Structure VII

Alternatively, the polymer conjugate may possess an overall forked structure. An example of a forked PEG corresponds to the following generalized structure, where the first structure represents an activated forked PEG and the second structure represents a forked NSAID polymer conjugate:

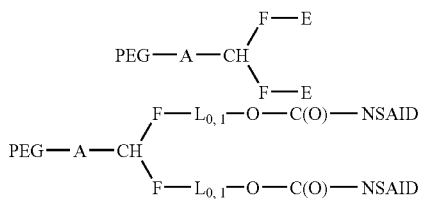

where PEG is any of the forms of PEG described herein, E is a reactive group suitable for covalent coupling with a NSAID such as hydroxyl, A is a linking group, preferably a hydrolytically stable linkage such as oxygen, sulfur, or —C(O)—NH—, F and F' are hydrolytically stable spacer groups that are optionally present. In the conjugate structure to the right, the NSAIDs can be the same or different. Although not shown explicitly, also contemplated is a forked structure where one of the NSAIDs is replaced by a non-NSAID, such as a proton pump inhibitor, or sumitriptan, or a weak opioid, or a synthetic prostaglandin E1 analog, or any other drug that may advantageously be co-administered with a NSAID of the invention. Exemplary linkers and spacer groups corresponding to A, F and F' are described in U.S. Pat. No. 6,362,254, and are useful in forming polymer conjugates in accordance with the present invention. F and F' are spacer groups that may be the same of different. In one particular embodiment of the above, PEG is mPEG, A corresponds to —C(O)—NH—, and F and F' are both methylene or —CH$_2$—. This type of polymer segment is useful for reaction with two active agents, where the two active agents are positioned at a precise or predetermined distance apart, depending upon the selection of F and F'.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable linkages include but are not limited to ester, carbonate ester, carbamate, sulfate, phosphate, acyloxyalkyl ether, acetal, and ketal. Such linkages when contained in a given polymer segment will preferably be stable upon storage and upon initial administration.

More particularly, as described generally above, two or more polymer segments connected by a hydrolyzable linkage may be represented by the following structure: PEG1-W-PEG2 (where PEG1 and PEG2 can be the same or different) and W represents a weak, hydrolyzable linkage. These polymer structures contain PEG segments that are removable (i.e., cleavable) in vivo, as described in detail in U.S. Patent Application Publication No. US 2002/0082345.

The PEG polymer used to prepare a conjugate of the invention may comprise a pendant PEG molecule having reactive groups, such as hydroxyl, covalently attached along the length of the PEG rather than at the end of the PEG chain(s). The pendant reactive groups can be attached to the PEG directly or through a spacer moiety, such as an alkylene group.

Additional representative PEGs having either linear or branched structures for use in preparing the conjugates of the invention may be purchased from Nektar Therapeutics, Huntsville Division (formerly Shearwater Corporation, Huntsville, Ala.). Illustrative structures are described in Nektar's 2004 and 2005-2006 catalogs, the contents of which are expressly incorporated herein by reference.

Hydrolytically degradable linkages, useful not only as a degradable linkage within a polymer backbone, but preferably in the case of the instant invention, for covalently attaching a polymer to a NSAID, optionally via an intervening linker include the following: carbonate; imine resulting, for example, from reaction of an amine and an aldehyde (see, e.g., Ouchi et al. (1997) *Polymer Preprints* 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and certain urethane linkages.

Additional PEG reagents for use in the invention include hydrolyzable PEGs and linkers such as those described in International Patent Application Publication No. WO 04/089280. In utilizing this approach, one or more of the free functional groups within a NSAID as described herein is derivatized with a group sensitive to mild basic conditions, e.g., 9-fluorenylmethoxycarbonyl (Fmoc) or 2-sulfo-9-fluorenylmethoxycarbonyl (FMS), that is covalently attached to a polymer segment such as a PEG moiety. In the resulting conjugate, the NSAID and the polymer are each covalently attached to different positions of the scaffold Fmoc or FMS structure, and are releasable under physiological conditions.

Such optional features of the polymer conjugate, i.e., the introduction of one or more degradable linkages into the polymer chain, may provide for additional control over the final desired pharmacological properties of the conjugate upon administration. For example, a large and relatively inactive conjugate (i.e., having one or more high molecular weight PEG chains attached thereto, for example, one or more PEG chains having a molecular weight greater than about 10,000, wherein the conjugate possesses essentially no or insignificant bioactivity) may be administered, such that in vivo hydrolysis generates a bioactive NSAID conjugate possessing a portion of the original PEG chain. Alternatively, if a degradable linkage is used to covalently attach the NSAID to the polymer, hydrolysis results in the original NSAID absent the polymer segment, or alternatively, a modified NSAID possessing a short tag portion left over from hydrolysis of the polymer segment, where the modified NSAID still retains its therapeutic properties. In this way, the properties of the conjugate can be more effectively tailored to balance the pharmacological properties of the conjugate upon administration.

Those of ordinary skill in the art will recognize that the foregoing discussion concerning substantially water-soluble polymer segments is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

Conjugate Preparation, Linkages and Compositions

As described above, a conjugate of the invention comprises a water-soluble polymer, POLY, covalently attached to a NSAID. Typically, for any given conjugate, there will be one or more NSAIDs covalently attached to the water-soluble polymer, where the polymer may possess any of the forms described herein. In a preferred embodiment, the conjugate possesses 1 to 10 NSAIDs covalently attached to the water-soluble polymer, e.g., 1, 2, 3, 4, 5, 6, 7, 8, 9, or 10.

The particular linkage covalently attaching the NSAID to the polymer depends on a number of factors. Such factors include, for example, the particular linkage chemistry employed, the particular NSAID, the available functional groups for covalent attachment within the NSAID, the potential presence of additional reactive functional groups within the NSAID that may optionally require protecting groups, and the like.

The conjugates of the invention can be, although are not necessarily, prodrugs, meaning that the linkage between the polymer and the NSAID is hydrolytically degradable to allow release of the parent NSAID moiety. Such linkages can be readily prepared by appropriate modification of either the NSAID and/or the polymeric reagent using coupling methods commonly employed in the art combined with the teachings of the present application. Most preferred, however, are hydrolyzable linkages that are formed by reaction of a suitably activated polymer with a non-modified functional group contained within the NSAID such as a carboxyl group, optionally via an intervening linker.

Alternatively, a hydrolytically stable linkage, such as an amide, urethane (also known as carbamate), amine, thioether (also known as sulfide), or urea (also known as carbamide) linkage can also be employed as the linkage for coupling the NSAID. One preferred hydrolytically stable linkage is an amide.

The conjugates (as opposed to an unconjugated NSAID) may or may not possess a measurable degree of pharmacological activity, depending upon whether the polymer is covalently attached via a degradable or a hydrolytically stable linker. That is to say, a polymer conjugate in accordance with the invention will possess anywhere from about 0.1% to about 100% or more of the pharmacological activity of the unmodified parent NSAID. Preferably, conjugates possessing little or no activity contain a hydrolyzable linkage connecting the polymer to the NSAID, so that regardless of the lack of activity in the conjugate, the active NSAID (or a derivative thereof) is released upon aqueous-induced cleavage of the hydrolyzable linkage.

For conjugates possessing a hydrolytically stable linkage that couples the NSAID to the polymer, the conjugate will most preferably possess a measurable degree of the pharmacological activity associated with the unmodified parent NSAID. For instance, such polymer conjugates are typically characterized as having an activity of at least about 2%, 5%, 10%, 15%, 25%, 30%, 40%, 50%, 60%, 80%, 85%, 90%, 95% 97%, 100%, or more relative to that of the unmodified parent NSAID, when measured in a suitable in vivo or in vitro model, such as those well known in the art. (See, e.g., Kato, M., et al., *J. Pharm. Pharmacol.*, 2001, December; 53(12): 1679-88). Preferably, conjugates having a hydrolytically stable linkage (e.g., an amide linkage) will possess at least some degree of the bioactivity of the unmodified parent NSAID.

Exemplary polymer conjugates can be prepared using, e.g., any of a number of commercially available polymer starting materials, such as those available from Nektar Therapeutics, Huntsville Division, DowPharma, PegShop (a division of SunBio), Sigma-Aldrich, and the like. The polymers can be used in their "as-purchased" form, or alternatively, may be transformed in one or more chemical transformations to a form suitable for coupling with an NSAID, optionally via an intervening linker. The catalogs of each of the above-described polymer suppliers are hereby incorporated herein by reference. In particular, segments of such catalogs pertaining to polymer or even more particularly PEG reagents, are hereby incorporated by reference.

There are a number of examples of suitable water-soluble polymeric reagents useful for forming covalent linkages with reactive carboxyl groups contained within the NSAID. Hydroxy-terminated PEGs are particularly advantageous.

Additionally, for certain embodiments of the invention directed to degradable NSAID conjugates, a commercially available polymer, if not in a form suitable to provide a hydrolyzable linkage, can be modified to form a conjugate comprising a degradable linkage as follows. For instance, a bifunctional spacer, preferably one that can be releasably attached to an NSAID, e.g., an amino alcohol, is covalently attached to a reactive site, e.g., a carboxyl group, on the NSAID. Preferably, the bifunctional spacer possesses at one end an amino group, such that reaction with an amino-reactive polymer reagent is readily promoted. At the other end of the bifunctional spacer is, for example, a hydroxyl group effective to form a hydrolyzable ester upon reaction with one or more hydroxyl groups present on the NSAID, such that upon hydrolysis, the polymer and spacer are cleaved, resulting in release of the parent NSAID drug.

Gel formulations employing polymers of the type described immediately above will be discussed in greater detail in the sections that follow.

Particular reaction conditions for coupling PEG to a NSAID will vary depending upon the NSAID, the presence of additional reactive functional groups in the NSAID, the desired degree of PEGylation, and the particular reagent being utilized. Typically, conjugation of a polymeric reagent to a NSAID is carried out at molar ratios of a monofunctional polymer reagent to NSAID of about 20:1 to about 1:1, depending upon the reactivity of the polymer reagent employed. Suitable molar ratios are typically selected from the following: 20:1, 10:1, 7:1, 5:1, 2.5:1, 2:1, 1.1:1, and 1:1. For multi-armed polymer reagents possessing more than one reactive functional group for covalent attachment to drug, the molar ratios can be based upon polymer reagent or polymer reactive group. For multi-armed polymer reagents per se, typically an excess of NSAID is employed to promote reaction at each polymer arm, to thereby increase the yield of fully-coupled conjugate product. For example, for a 4-armed polymer reagent, where each polymer arm possesses a reactive group for coupling, a typical polymer reagent to NSAID ratio is 1:4 (i.e., one polymer having four arms, each arm reacting with drug). More preferably, the molar ratio of reactants is selected from $1_{polymer}:5_{NSAID}$, 1:6, 1:7, 1:8, 1:9, 1:10, 1:15, or 1:20 or greater, such that a molar excess of drug relative to polymer is employed. Typically, when employing a multi-armed reagent, a molar excess of NSAID such as the following is employed: a 1.5 molar excess, a 2-fold molar excess, a 2.5-fold molar excess, a 3-fold molar excess, a 4-fold molar excess, a 5-fold molar excess, a 7-fold molar excess, a 10-fold molar excess, or even a 20-fold molar excess. Unreacted drug is typically recovered from the reaction mixture using conventional separation techniques such as extraction, chromatography, and the like.

Generally, the coupling reaction is carried out in an organic solvent or solvent system. Suitable solvents include chloroform, dichloromethane, toluene and other aromatic hydrocarbons, acetonitrile, acetone, dioxane, dimethylformamide or tetrahydrofuran. The coupling reaction is preferably carried out under dry or anhydrous conditions, at temperatures ranging from about −15° C. to about 250° C., or from about 0° C. to about 200° C., or from about 25° C. to about 175° C. Anhydrous conditions are particularly preferred when forming ester-linked conjugates, to minimize the potential for hydrolysis, and thus reduced yields. The conjugation reaction is typically carried out in the presence of a coupling reagent, that is to say, a reagent effective to promote the coupling or conjugation of the desired reactants, such as a polymer reagent and a NSAID. The choice of a particular coupling reagent will depend upon the particular functional groups to be reacted. Exemplary coupling reagents include dicyclohexylcarbodiimide (DCC) (H. Ogura, et al. (1979) *Tetrahedron Lett.*, 20, 4745; H. Ogura, et al. (1981) *Tetrahedron Lett.*, 22, 4817); 4-dimethylaminopyridine (DMAP), used as a catalyst for esterification and amidation reagents (Takeda, K., et al. (1991), *Synthesis*, 1991, 689); N-hydroxybenzotriazole (HOBT) (W. Koenig, et al. (1970) *Chem. Ber.*, 103, 788; W. Koenig, et al. (1973) *Chem. Ber.*, 106, 3626; K. Barlos, et al. (1985) *J. Org. Chem.*, 50, 696); benzotriazole-1-yl-oxy-tris-(dimethylamino)-phosphoniumhexafluorophosphate (BOP) (B. Castro, et al. (1975) *Tetrahedron Lett.*, 16, 1219); (H. Ogura, et al. (1979) *Tetrahedron Lett.*, 20, 4745; H. Ogura, et al. (1981) *Tetrahedron Lett.*, 22, 4817); and N-hydroxysuccinimide, NHS (G. W. Anderson, et al. (1964) *J. Am. Chem. Soc.*, 86, 1839; F. Weygand, et al. (1966) *Z. Naturforsch.*, 21, 426). These and other suitable coupling reagents are commercially available from various sources such as NovaBiochem. The polymer reactant and NSAID, along with any other necessary reagents, are typically reacted from about 0.5 hours to forty-eight hours, or until completion of the reaction is determined using an appropriate analytical monitioring technique, such as nuclear magnetic resonance spectroscopy, gas or liquid chromatography, thin layer chromatography, or the like. Preferably, the coupling reaction is carried out under a dry, inert atmosphere (e.g., $N_2$ or Ar).

Following conjugation, the product is isolated, for example, by extraction, filtration, removal of solvent (e.g., by rotary evaporation, lyophilization or distillation), or precipitation, or any combination thereof. The recovered product may be analyzed, for example, by gel permeation chromatography, to determine the extent of conjugation.

The crude product can be further purified if desired by any suitable technique, such as ion exchange chromatography or reverse phase HPLC.

As described previously, linkage between the NSAID and the polymer preferably results from the reaction between a polymer reagent bearing a terminal functional group and a carboxyl-containing NSAID. The specific linkage will depend on the type of functional group utilized. If the polymer is end-functionalized or "activated" with a hydroxyl group, the resulting linkage will be a carboxylic acid ester. If the polymer is functionalized with a thiol group, the resulting linkage will be a thioester Water-soluble derivatives containing a hydrazide moiety are also useful for conjugation at carboxyl groups. An example of such a derivative includes a polymer having the following structure:

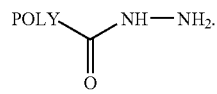

Typically, although not necessarily, the optional linkage between the NSAID and the polymeric reagent includes one or more atoms such as one or more of carbon, nitrogen, sulfur, and combinations thereof. For instance, preferred hydrolytically stable linkages comprise an amide, secondary amine, carbamate, thioether, or disulfide group. Optionally, additional atoms can connect the linkage to the chain of repeating monomers within the polymeric reagent. The same holds true for embodiments wherein the linkage is degradable, i.e, comprises a hydrolytically degradable moiety. Typically, the degradable linkage, when considered overall, contains additional atoms or combinations of atoms connecting the degradable moiety per se to the polymer and/or the NSAID. Non-limiting examples of specific series of atoms connecting the drug to the chain of repeating monomers designated herein as POLY include those selected from the group consisting of —O—, —S—, —S—S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —O—CH$_2$—

—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—$CH_2$—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —O—C(O)—NH—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —O—C(O)—NH—$[CH_2]_{0-6}$—$(OCH_2CH_2)_{0-2}$—, —C(O)—NH—$(CH_2)_{1-6}$—NH—C(O)—, —NH—C(O)—NH—$(CH_2)_{1-6}$—NH—C(O)—, —O—C(O)—$CH_2$—, —O—C(O)—$CH_2$—$CH_2$—, and —O—C(O)—$CH_2$—$CH_2$—$CH_2$—.

Additionally, bifunctional linkers such as amino acids or difunctional PEG oligomers may be used to connect the drug to the polymer reagent. Preferably, a linker is aliphatic rather than aromatic, and is typically although not necessarily linear rather than branched.

The conjugates are typically part of a pharmaceutical composition. The composition will typically contain a single type of polymer conjugate, e.g., a discrete PEG-NSAID conjugate, or may contain a plurality of conjugates, for example, having slightly different chemical structures. In one such embodiment, e.g., of a multi-armed polymer conjugate, a composition prepared from a 4-armed polymer reagent may contain a mixture of polymer conjugates having one, two, three and/or four NSAIDs covalently attached to the polymer. Such a composition can be administered as such, or may be further purified or fractionated to contain only one discrete chemical entity (e.g., a polymer conjugate having a drug covalently attached to each polymer arm), or to provide desired combinations of conjugates (e.g., a 4-arm polymer having drug attached to each arm, in combination with a polymer having drug attached to only three of the four polymer arms, and so forth).

As discussed briefly above, control of the desired number of drugs to be covalently attached to any given polymer reagent can be achieved by selecting the proper polymeric reagent, the ratio of polymeric reagent to NSAID, temperature, pH conditions, solvent, and other aspects of the conjugation reaction. In addition, reduction or elimination of the undesired conjugates can be achieved using conventional purification methods.

Additional Multi-Armed Polymer Conjugates

Multi-armed polymers for use in forming conjugates having multiple NSAIDs or other agents covalently attached thereto have been described previously herein. Multi-armed polymers are particularly attractive in cases where high doses of the NSAID are required to deliver a therapeutically effective amount, e.g., of an NSAID such as ketorolac. In this way, drug is "loaded up", preferably releasably, onto a single polymer molecule having several reactive sites suitable for covalent attachment.

One preferred type of multi-armed polymer for achieving maximal NSAID loading is a multi-arm block copolymer having an inner core region defined by a central core molecule having polypeptide segments covalently attached thereto and an outer hydrophilic region defined by hydrophilic polymer segments covalently attached to each of the polypeptide polymer segments. Thus, each arm of the multi-arm structure is a block copolymer comprising an inner (i.e. closer or proximal to the central core molecule) polypeptide polymer segment and an outer (i.e. further or distal from the central core molecule) hydrophilic polymer segment. Such multi-arm block copolymers are particularly well suited for encapsulation or entrapment of biologically active molecules within the inner core region. As used in the present context, "encapsulation" or "entrapment" is intended to refer to the physical confinement of a NSAID within the inner core region of the copolymer, whether by covalent attachment, charge interaction, metal-acid complex, van der Waals forces, or other attraction or bonding force. Such unimolecular multi-arm block copolymers typically have a total number average molecular weight of from about 5,000 Da to about 120,000 Da, preferably from about 10,000 Da to about 100,000 Da, and more preferably from about 20,000 Da to about 80,000 Da.

The outer hydrophilic polymer segments are preferably poly(ethylene glycol), although other hydrophilic polymer segments can also be used. The use of a polypeptide polymer segment as part of the inner core region of the unimolecular multi-arm structure provides tremendous flexibility in designing and adjusting the drug delivery properties of the multi-arm structure. Interaction between a NSAID and the core region of the unimolecular multi-arm structure can greatly affect drug loading and drug release characteristics. In the present invention, depending on the structure of the polypeptide polymer segments, the inner core region can be hydrophobic, charged, suitable for covalent attachment to drug molecules, or any combination thereof.

Preferably, the central core molecule is a residue of a polyamine having at least three termini bearing an amine group. The use of a polyamine core is preferred because the amine groups of the core readily react with the carboxylic acid group of an amino acid to form an amide linkage. Core molecules having other functional groups available for attachment to the copolymer arms can, however, also be used. In embodiments utilizing a polyamine core, the number of amine groups will dictate the number of copolymer arms in the multi-arm structure. Preferably, the polyamine comprises from 3 to about 25 amine groups. In various embodiments, the polyamine comprises at least about 5 amine groups, at least about 8 amine groups, or at least about 10 amine groups. Multi-armed polymers having these types of structures are described in detail in co-owned patent application entitled, "Multi-Arm Polypeptide Poly(ethylene Glycol) Block Copolymers as Drug Delivery Vehicles", filed on Dec. 24, 2003, which corresponds to International Patent Application Publication No. WO/04060977, the contents of which are expressly incorporated herein by reference.

Illustrative polymer structures include multi-arm (3, 4, 5, 6, 7, 8, 9, 10, 11 or 12-arm) poly(benzyl aspartate)-PEG, poly(aspartic acid)-PEG having multiple NSAIDs covalently attached to the polypeptide core of the structure, preferably although not necessarily via degradable linkages such as ester and hydrolyzable carbamate. Alternatively, rather than being covalently attached, a NSAID may be entrapped within the inner core region.

In yet another embodiment, a multi-armed block copolymer for use in preparing an NSAID composition possesses a central core molecule, such as a residue of a polyol, and at least three copolymer arms covalently attached to the central core molecule. Each copolymer arm comprises an inner hydrophobic polymer segment covalently attached to the central core molecule and an outer hydrophilic polymer segment covalently attached to the hydrophobic polymer segment. The block copolymer provides a unimolecular micelle structure, wherein the central core molecule and the hydrophobic polymer segment define a hydrophobic core region and the hydrophilic polymer segment defines an outer hydrophilic region. The solubility of hydrophobic biologically active agents such as NSAIDs can be improved by entrapment within the hydrophobic core region of the block copolymer. Preferably, the central core molecule of the multi-arm block copolymer structure is the residue of a polyol having at least three hydroxyl groups available for polymer attachment. Depending on the desired number of copolymer arms, the polyol will typically comprise 3 to about 25 hydroxyl groups, preferably at least 5, more preferably at least about 8, and most preferably at least about 10. Preferred polyols include glycerol, reducing sugars such as sorbitol, pentaerythritol, glycerol oligomers, such as hexaglycerol, and hydroxypropyl-β-cyclodextrin, which has 21 available hydroxyl groups. Preferred hydrophobic polymer segments for use in such compositions include poly(hydroxyesters) such as poly(lactide), poly(glycolide), poly(lactide/glycolide) copolymer, poly(butyrolactide) and polycaprolactone, and poly(alkylene oxides) other than poly(ethylene glycol), such as poly(propylene oxide) (PPO) or poly(butylene oxide) (PBO), or copolymers thereof. The hydrophilic polymer segment is preferably, poly(ethylene glycol) (PEG). Representative polymer delivery systems such as these are described in co-owned U.S. Pat. No. 6,730,334.

Hydrogels

In contrast to the conjugate or covalently attached NSAID compositions previously described, additionally provided herein are hydrogel-NSAID compositions where the NSAID is not necessarily covalently attached to the polymer component(s), which are present in the form of a gel (or a dehydrated precursor thereof). Such hydrogels can be cross-linked or non-cross-linked, and preferably contain a PEG-component. In one particular embodiment, the hydrogel components are non-cross-linked or are lightly crosslinked to facilitate release of the NSAID. The NSAID may be present in conjugated and/or unconjugated form.

An illustrative hydrogel possesses an aromatic-hydrolyzable carbamate segment. In particular, the hydrogel is composed of a polymer bonded to a crosslinking agent through a hydrolyzable carbamate linkage as described in co-owned U.S. Pat. No. 6,514,491. Typically, the polymer backbone is any compound having an amino group, preferably at least two amino groups. Examples of such backbones include, but are not limited to, proteins, peptides, aminocarbohydrates, aminolipids, poly(vinylamine), polylysine, poly(ethylene glycol) amines, pharmaceutical agents having an amino group, etc. The crosslinking agent in a preferred embodiment is a difunctional polymer having the formula:

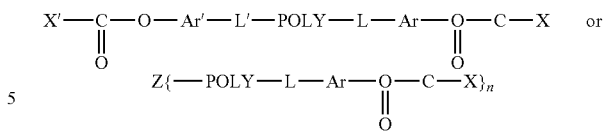

wherein POLY is a non-peptidic, water soluble polymer such as PEG, L and L' are linking groups such as —O— or —NH—C(O), Ar and Ar' are aromatic groups such as an ortho, meta, or para-substituted phenyl, Z is a central branch core, n is from 2 to about 100, and X and X' are activating groups capable of reacting with the amino groups in the backbone to form hydrolyzable carbamate linkages.

In a preferred embodiment, the crosslinking agent has the formula:

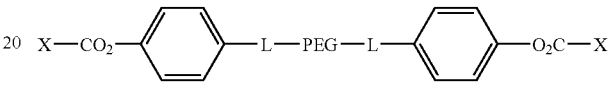

wherein X and L are as described above. Thus, the crosslinking of a polymer having multiple amino groups with the above crosslinking agent is illustrated below:

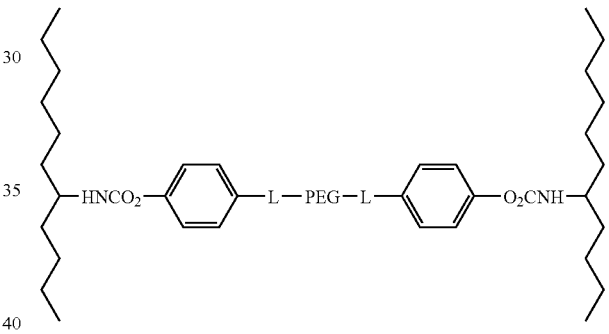

where the zig-zag notation represents a polymer having amine groups and where L is as described above.

As will be apparent, the carbamate linkages between the polymer portions and the crosslinker are hydrolyzable. Thus, this hydrogel gradually breaks down or degrades in the body as a result of the hydrolysis of the carbamate linkages.

Another type of advantageous hydrogel for preparing a NSAID composition possesses carbonate linkages. More particularly, provided is a a water soluble, nonpeptidic polymer composed of two or more oligomers linked together by hydrolytically degradable carbonate linkages, as described in co-owned U.S. Pat. No. 6,348,558, the contents of which is expressly incorporated herein by reference. The polymer can be hydrolytically degraded into small oligomers in an aqueous environment, e.g., in vivo, and can be used to prepare degradable hydrogels.

A representative polymer of this sort is represented by the formula: X—O—[(—CH$_2$CH$_2$—O—)$_n$—CO$_2$—]$_m$—(CH$_2$CH$_2$O)$_n$—Y, where n is an integer of from about 2 to about 2,000, m is an integer of from about 2 to about 200, and where X and Y each independently is H, alkyl, alkenyl, aryl, or a reactive moiety, and can be same or different. In the instance where either X or Y (or both) is reactive with a functional group of the NSAID, then the NSAID may optionally be covalently attached thereto in yet another embodiment of the invention.

In yet another embodiment, a hydrogel for use in preparing a NSAID composition is a thiosulfonate gel as described in co-owned PCT Application No. WO 04/060967 entitled, "Methods for the Formation of Hydrogels Using Thiosulfonate Compositions and Uses Thereof", filed in the United States on Dec. 31, 2003, the content of which is expressly incorporated herein by reference More particularly, in accordance with this embodiment of the invention, hydrogel forming components are preferably multi-arm thiosulfonate polymer derivatives that form a crosslinked polymer composition when exposed to base, without requiring the presence of a second cross-linking reagent, redox catalyst, or radiation. Such thiosulfonate polymer derivatives can also form a hydrogel by reaction with a water-soluble polymer having at least two thiol groups.

Generally, such compositions comprise hydrogel-forming components corresponding to the formula below:

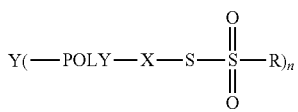

where POLY is a water-soluble polymer, n ranges from 3 to about 100, X is a linking group, Y is a moiety derived from a molecule having at least three nucleophilic groups, and R is an alkyl or aryl group. Exemplary linking groups are described elsewhere herein. The polymer may optionally contain at least one degradable linkage, e.g., an ester, carbonates acetal, orthoester, phosphate, or thiolester. The presence of one or more degradable linkages allows for the degradation of the polymer chains (e.g., by hydrolysis or enzymatic degradation) with concomitant breakdown and dissolution of the hydrogel. In a preferred embodiment, the hydrogel or polymer containing composition effective to form a hydrogel is one which does not exhibit reverse gelation properties, i.e., exists as a liquid below physiological temperature but which forms a hydrogel at physiological temperature.

Other suitable hydrogels and hydrogel-forming materials include photocrosslinkable hydrogels prepared from glycidyl methacrylate hyaluronic acid and acrylated PEG as described in Leach, J. B., et al., "*Development of photocrosslinkable hyaluronic acid-polyethylene glycol-peptide composite hydrogels for soft-tissue engineering*", Wiley InterScience, 13 May 2004 (published online), thermoreversible gels obtained by polymerization of saccharide monomers as described in U.S. Pat. No. 6,018,033, photopolymerizable, biodegradable hydrogels based on e.g., PEG-oligoglycolylacrylate monomers, as described in U.S. Pat. No. 6,602,975, and the like. Each of the hydrogels contains an NSAID as described herein, contained within the hydrogel matrix. The NSAID can by entrapped within the matrix and/or covalently attached thereto, and may optionally be in the form of a water-soluble polymer conjugate as described herein.

Hydrogel compositions of the invention can be prepared prior to use. Formed hydrogel compositions may optionally be subject to dehydration or lyophilization in order to remove bound water and used as either the intact hydrogel or reduced to powder or particulate form. Hydrogel compositions of the invention may also be employed without dehydration or lyophilization as formed objects or maybe incorporated into delivery systems including without limitation: ocular inserts, implants, suppositories, pessaries, transdermal patches, or capsules filled with the hydrogel compositions. In a preferred embodiment, the compositions herein are used to locally apply or administer an NSAID to a particular tissue surface or intended site of action.

Regardless of the form of the hydrogel forming composition or hydrogel composition, it is possible to package the compositions in single use, multiple use or bulk containers. The preparations may optionally be sterilized by art-recognized procedures. In one preferred embodiment, the materials are packaged in sterile single use containers. In other embodiments, the materials are packaged for ease of reconstitution by addition of water, aqueous solutions or suspensions in single or multiple use containers. In another embodiment, the materials are sold as a kit with a base or other suitable initiator to initiate gel formation.

Purification of Conjugates

The polymer-NSAID conjugates of the invention can be purified to obtain/isolate different conjugated species, if appropriate. The strategy for purification of the final conjugate reaction mixture will depend upon a number of factors, including, for example, the molecular weight of the polymeric reagent employed, the particular NSAID, the desired dosing regimen, and product mixture, and the residual activity and in vivo properties of the individual conjugate(s).

Suitable purification techniques include recrystallization, various types of chromatographic separations such as gel filtration chromatography, ion exchange chromatography, and/or reverse phase chromatography.

Assessment of Activity

The bioactivity of the conjugates and compositions of the invention may be determined using known in vivo or in vitro models, depending upon the known activities of the particular NSAID employed. Models for determining the activity of a NSAID conjugate or composition in the treatment of acute pain include the following. For use in the treatment of acute pain, various well-established models may be employed to assess the efficacy of a conjugate of the invention, e.g., in a clinical trial. Such models include the postoperative pain model (e.g., in surgeries such as postorthopedic, postgeneral, and postgynecological), the oral surgery model (which focuses on the extraction of impacted third molars) and the dysmenorrhea model. For in vivo studies in humans, categorical or visual analog scales are typically used to standardize pain scores. Commonly employed categorical scales include (i) a four point measure of pain intensity, with 0=no pain, 1=mild pain, 2=moderate pain, and 3=severe pain, and (ii) a five-point measure of relief where 0=no relief, 1=a little relief, 2=some relief, 3=a lot of relief and 4=complete relief (Sunshine, A. Metholodology of analgesic clinical trials. *Am. J. Orthoped.*, 27:S12-S16 (1998)). Animal models may also be employed to assess post-operative pain, such as the pain-induced functional impairment model in the rat (Abram, S., *Anesthesiology*: Vol 86(5), May 1997, p 1015-1017 and references cited therein; Granados-Soto, V., et al., *Pharmacology and Experimental Therapeutics,* 1995, 272 (1), 352-356). Animal models for investigating the ability of a conjugate of the invention to 'spare' the gastrointestinal tract, i.e., its ability to reduce associated gastric toxicity upon administration, may also be used. See, for example, Davies, N. M., et al., (1997) *Aliment. Pharmacol. Ther.* 11:69-79; Wallace, J. L., et al., *Eur. J. Pharmacol.* 280: 63-68 (1995a); Wallace J. L., et al., *Am. J. Physiol* 273: G1246-G1252, (1997)). Such studies examine damage such as lesions to the rat stomach, damage to the jejunum/ileum and small intestine, and assessment of haematocrit and gastrointestinal bleeding.

Pharmaceutical Compositions

Optionally, the compositions of the invention may further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form); fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the NSAID and the polymeric reagent) or NSAID itself (e.g., when contained in a drug delivery system such as a hydrogel of micellular-based system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the conjugate or composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use.

Preferably, the NSAID compositions described herein are in unit dosage form, meaning an amount of a conjugate or composition of the invention appropriate for a single dose, in a premeasured or pre-packaged form.

The NSAID compositions herein may optionally include one or more additional active agents. Particularly preferred are compounded preparations including active agents such as epinephrine, dexamethasone, lidocaine, bupivacaine, phenylbutazone, cyclobenzapine, carbamazepine, amitryptyline, and capsaicin. Alternatively, such agents can be co-administered rather than contained in an NSAID-composition of the invention.

Administration

The compositions of the present invention are typically, although not necessarily, administered orally, via injection (intravenously or intramuscularly), or locally. In a particular embodiment, a composition of the invention is used for localized delivery of a NSAID, for example, for the treatment of post-operative pain. In particular, the compositions described herein are useful in post-operative pain associated with postorthopedic (e.g., joint replacement), postgeneral, and post gynecological surgeries, among others. Additionally, the compositions herein are useful for reducing postsurgical pain including oral and abdominal surgeries. Local sustained delivery of NSAIDs provides effective local concentrations of active agent near the site of effect, while keeping systemic levels relatively low. Low systemic levels of the NSAID are particularly advantageous, since adverse side effects often result from the high systemic doses required to achieve a local effect.

The pharmaceutical preparation can be in any form suitable for delivery, e.g., a liquid solution or suspension immediately prior to administration, a syrup, cream, ointment, tablet, capsule, powder, gel, matrix, or the like, depending upon the mode of delivery. Additional modes of administration are also contemplated, such as pulmonary, rectal, transdermal, transmucosal, intrathecal, pericardial, subcutaneous, intra-arterial, intracerebral, intraocular, and so forth.

The invention also provides a method for administering a conjugate as provided herein to a patient suffering from a condition that is responsive to treatment with the NSAID contained in the conjugate or composition. The method comprises administering, via any of the herein described modes, a therapeutically effective amount of the conjugate or drug delivery system, preferably provided as part of a pharmaceutical composition. In a preferred embodiment, a composition of the invention is injected at one or more sites proximal to the surgery site.

The method of administering may be used to treat any condition that is responsive to treatment with a NSAID. More specifically, the compositions herein are effective in treating inflammation, providing moderate to severe pain relief (e.g., post-surgery), and are effective, in certain cases, as cancer chemotherapeutic and chemopreventive agents, particular in the and prevention of colon, breast and bladder cancer (Koki, A T, et al., *Expert Opin Investig Drugs,* 8:1623-38 (1999); Reddy, B S et al., *Cancer Res.* 2000, 60, 2293-2297; Davies, G., et al., *Annal Oncol.,* 2002, 13:669-78). The compositions of the invention are advantageous in the treatment of inflammatory and painful conditions such as rheumatoid arthritis, gout, bursitis, painful menstruation, headache, and inflammation associated with cataract extraction.

Those of ordinary skill in the art appreciate which conditions a specific conjugate (e.g., containing a particular NSAID) can effectively treat. The actual dose to be administered will vary depend upon the age, weight, and general condition of the subject as well as the severity of the condition being treated, the judgment of the health care professional, and conjugate (i.e., NSAID) being administered. Therapeutically effective amounts can be determined by those skilled in the art, and will be adjusted to the particular requirements of each particular case. Generally, a therapeutically effective amount will range from about 0.05 mg to 5 grams NSAID daily, more preferably from about 0.5 mg to 2 grams daily, even more preferably from about 7 mg to 1.5 grams daily, even more preferably from about 0.05 mg to 750 mg. Preferably, such doses are in the range of 10-600 mg four times a day (QID), 200-500 mg QID, 25-600 mg three times a day (TID), 25-50 mg TID, 50-100 mg TID, 50-200 mg TID, 300-600 mg TID, 200-400 mg TID, 200-600 mg TID, 100 to 700 mg twice daily (BID), 100-600 mg BID, 200-500 mg BID, or 200-300 mg BID. In cases in which a therapeutic composition of the invention is administered locally, the dose administered is preferably significantly reduced in comparison to a typical systemic dose. For example, preferably, the dose of a conjugate of the invention, when administered locally, is typically reduced to about 75% or less of the typical systemic dose, to about 60% or less of the typical systemic dose, to about 50% or less of the typical systemic lose, to about 40% or less of the typical systemic dose, to about 30% or less of the typical systemic dose, to about 20% or less of the typical systemic dose, or most preferably, to about 10% or less of the typical systemic dose. Preferred dosage ranges for locally administered conjugates are from about 5-50% of the typical systemic dose, or from about 5-30%, or even more preferably from about 5 to 20% of the typical systemic dose.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred conjugate and compositions are those requiring dosing less frequently than once a day. That is to say, preferably, the composition of the invention is administered twice daily, once daily, once every other day, twice a week, once a week, once every two weeks, or once a month. Even more preferred are conjugates and compositions that are administered no more frequently than once a week, even more preferably no more frequently than twice monthly (every two weeks).

One advantage of administering certain conjugates of the present invention is that individual water-soluble polymer portions including the entire polymer can be cleaved. Such a result is advantageous when clearance from the body is potentially a problem because of the polymer size. Optimally, cleavage of each water-soluble polymer portion is facilitated through the use of physiologically cleavable and/or enzymatically degradable linkages such as carbonate or ester-containing linkages. In this way, clearance of the conjugate (via cleavage of individual water-soluble polymer portions) can be modulated by selecting the polymer molecular size and the type functional group that provides the desired clearance properties. One of ordinary skill in the art can determine the optimal molecular size of the polymer as well as the cleavable functional group. For example, one can determine a preferred polymer molecular size, structure, and/or cleavable functional group by preparing a variety of polymer derivatives with different polymer weights and cleavable functional groups, and then conducting in vitro or in vivo assays as described herein to assess efficacy. Alternatively, clearance profiles may be obtained (e.g., through periodic blood or urine sampling) using suitable in vivo models.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

ABBREVIATIONS

Boc t-butyloxycarbonyl
DCC dicyclohexylcarbodiimide
DCM dichloromethane
DI deionized
DIC 1,3-diisopropylcarbodiimide
DMAP 4-dimethylaminopyridine
HOBT 1-hydroxybenzotriazole
IPA isopropyl alcohol
PBS phosphate buffered saline
PEG polyethylene glycol
PG polyglutamic acid
PTSA p-toluenesulfonic acid
RT room temperature TEA triethylamine
Teoc 2-trimethylsilylethyl carbamate
Troc 2,2,2-trichloroethylcarbamate
trt trityl
TFA trifluoroacetic acid
4-arm PEG-OH

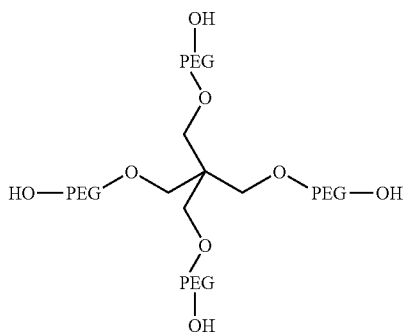

EXAMPLES

Materials 4-arm PEG-20K and 4-arm PEG 40K were obtained from Nektar, Huntsville, Ala. Division. All other PEG reagents referred to in the appended examples are available from Nektar, Huntsville, Ala., unless otherwise indicated. HOBT and DMAP were purchased from Aldrich. DCC was purchased from EM Science. All other chemical reagents referred to in the appended examples are commercially available or can be prepared based on information available in the art unless otherwise indicated.

$^1$H NMR data was generated by a 300 or 400 MHz NMR spectrometer manufactured by Bruker.

Example 1

Preparation of a 4-arm PEG (20K)-Ketorolac Delivery System

One gram (1.0 g) of ketorolac tris salt was converted to ketorolac by dissolution in 15 mL DI H$_2$O, followed by addition of 30 mL 1N HCl. The resulting solution was stirred until a white solid precipitated. The product was collected by filtration, dried under vacuum, and used in the following synthetic transformations.

4-arm-PEG-20K (2.0 g, MW=20 kDa), ketorolac (151 mg), HOBT (11 mg), DMAP (73 mg) and DCC (413 mg) were dissolved in anhydrous CH$_2$CL$_2$ (80 mL) to form a yellow solution which was then stirred at RT overnight. The resulting reaction mixture was filtered to remove any undissolved solids, and the solvent removed by rotary evaporation. IPA (~200 mL) was then added to the remaining residue to precipate the product. The product was collected by filtration, and rinsed with ethyl ether. The recovered solid was dried under vacuum overnight. Yield of product (designated JY424, or 4-arm PEG-20K-KETO) was 95%. Based upon $^1$H NMR analysis, the drug loading amount was approximately 5% by weight.

Example 2

Preparation of a 4-arm PEG (40K)-Ketorolac Delivery System

Ketorolac was prepared from the corresponding tris salt as described in Example 1. 4-arm-PEG-40K (2.0 g, MW=40 kDa), ketorolac (76 mg), HOBT (6 mg), DMAP (37 mg) and DCC (207 mg) were dissolved in anhydrous CH$_2$CL$_2$ (80 mL) to form a yellow solution which was then stirred at RT overnight. The resulting reaction mixture was filtered to remove any undissolved solids, and the solvent removed by rotary evaporation. IPA (~200 mL) was then added to the remaining residue to precipate the product. The product was collected by filtration, and rinsed with ethyl ether. The recovered solid was dried under vacuum overnight. Yield of product (designated JY425 or 4-arm PEG-40K-KETO) was 94%. Based upon $^1$H NMR analysis, the drug loading amount was approximately 2.3% by weight.

Example 3

Release Study for 4-arm PEG Ketorolac

A release study was conducted to examine the release profiles of parent drug, ketorolac, from illustrative multi-arm polymer delivery systems to which the drug was covalently but releasably attached.

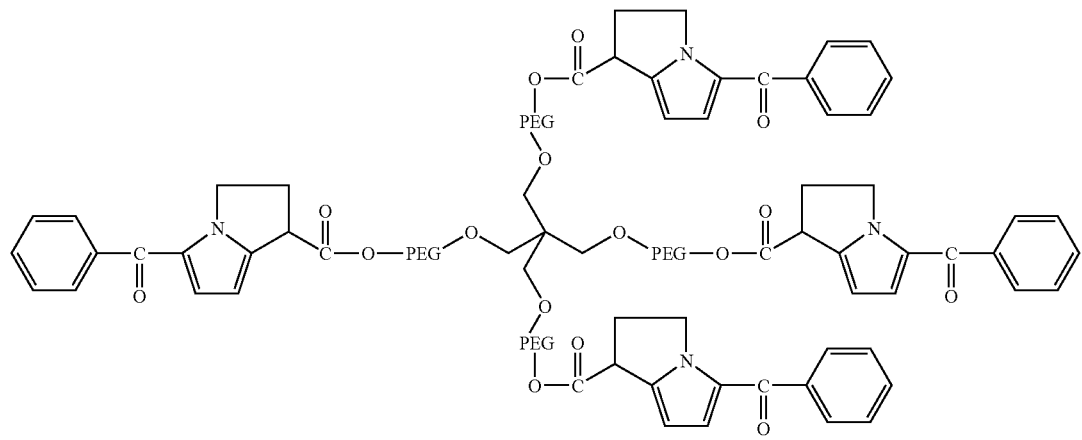

A. Sample Preparation:

4-arm PEG-20K KETO: 40.0 mg of 4-arm-20K-Ketorolac (JY424) was dissolved in 10 mL PBS, pH 7.4. After total dissolution, the solution was stored at 37° C. Analysis was based upon HPLC results. On the first day, two HPLC injections were carried out, thereafter, one injection was made daily to provide the release profile reported herein.

4-arm PEG-40K KETO: The sample was prepared in an identical fashion to 4-arm-20K-KETO.

B. Analytical Method

An HPLC method was employed to determine release profiles using a two-solvent gradient system. Solvent A was 0.1% TFA in $H_2O$; Solvent B was acetonitrile. A UV detector was employed at a wavelength of 280 nm. Release of unmodified parent drug from the delivery system was confirmed by NMR.

C. Results

As stated above, the kinetics of the reaction, i.e. the release rate of drug as a function of time, was measured for both 4-arm-PEG-20K-ketorolac and 4-arm PEG-40K-ketorolac in PBS buffer, at pH 7.4 at 37° C. Based upon the kinetic data, half-lives were determined for each of the illustrative conjugates. The half-life of the 4-arm-PEG-20K-ketorolac conjugate was 55 hours. The half-life of the 4-arm-PEG-40K-ketorolac conjugate was 43 hours.

Based upon the above, it can be seen that the half-lives of both of these conjugate-based delivery systems is approximately 2 days. The half-life of non-conjugated ketorolac is about 2 hours. Thus, the illustrative conjugate delivery systems described in these examples are effective to increase the half-life of ketorolac more than 5-fold; in the case of the 20 kD multi-armed PEG conjugate, the half-life of the drug is increased over 27 times, while in the case of the 40 kD multi-armed PEG conjugate, the half life of the drug is increased over 20 times.

A plot demonstrating the pharmacokinetics of these delivery systems is provided in FIG. 1.

What is claimed is:

1. A water-soluble polymer ketorolac conjugate having the structure:

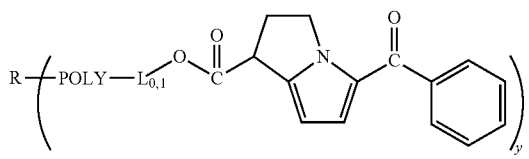

where:
R is an aliphatic polyol core molecule,
POLY is a water-soluble polymer,
L is an optional linker interposed between POLY and the carboxyl oxygen,
where $L_0$ indicates the absence of a linker and $L_1$ indicates the presence of a linker, and
y is an integer ranging from 3 to 8.

2. The conjugate of claim 1, where POLY is a homopolymer or a co-polymer.

3. The conjugate of claim 2, wherein POLY is selected from the group consisting of a poly(alkylene oxide), poly(vinyl pyrrolidone), poly(vinyl alcohol), polyoxazoline, and poly(acryloylmorpholine).

4. The conjugate of claim 3, wherein POLY is a poly(alkylene oxide).

5. The conjugate of claim 4, wherein the poly(alkylene oxide) is a poly(ethylene glycol).

6. The conjugate of claim 5, wherein the polyethylene glycol) has a molecular weight in a range selected from the group consisting of: from about 200 daltons to about 100,000 daltons, from about 500 daltons to about 75,000 daltons, from about 1,000 daltons to about 60,000 daltons, from about 2,000 daltons to about 50,000 daltons, and from about 5,000 daltons to about 45,000 daltons.

7. The conjugate of claim 6, wherein the polyethylene glycol) has a molecular weight selected from the group consisting of about: 100 daltons, 200 daltons, 300 daltons, 400 daltons, 500 daltons, 600 daltons, 700 daltons, 750 daltons, 800 daltons, 900 daltons, 1000 daltons, 1500 daltons, 2000 daltons, 2200 daltons, 2500 daltons, 3000 daltons, 4,000 daltons, 4,400 daltons, 5000 daltons, 6,000 daltons, 7,000 daltons, 7,500 daltons, 8,000 daltons, 9,000 daltons, 10,000 daltons, 11,000 daltons, 12,000 daltons, 13,000 daltons, 14,000 daltons, 15,000 daltons, and 20,000 daltons.

8. The conjugate of claim 1, wherein the linker is present and $L_1$ possesses a length selected from the group consisting of from about 1 to about 30 atoms, from about 2 to about 20 atoms, and from about 3 to about 15 atoms.

9. The conjugate of claim 1, wherein the linker is absent.

10. The conjugate of claim 1, wherein each POLY comprises a copolymer comprising an inner polypeptide segment covalently attached to the aliphatic polyol core molecule and an outer hydrophilic polymer segment covalently attached to said inner polypeptide segment.

11. The conjugate of claim 1, having a structure selected from the group consisting of:

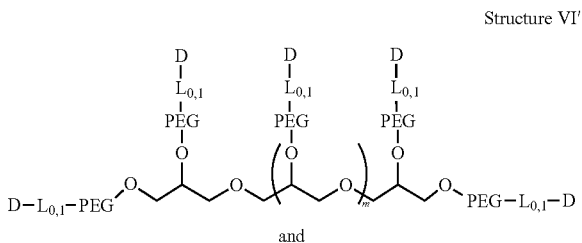

Structure VI' and

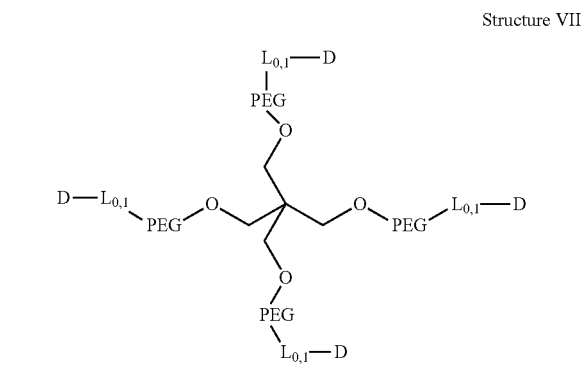

Structure VII wherein:
m is an integer selected from 3, 4, 5, 6, 7, and 8,
PEG is poly(ethylene glycol), and
D has the structure:

12. A pharmaceutical composition comprising a conjugate of claim 1.

13. A pharmaceutical composition of claim 12, further comprising a pharmaceutically acceptable excipient.

14. The conjugate of claim 8, wherein the linker is selected from an amino acid, an amino alcohol, and a bifunctional PEG oligomer.

15. The conjugate of claim 1, wherein the aliphatic polyol core molecule is selected from the group consisting of glycerol, pentaerythritol, sorbitol, and trimethylolpropane.

16. The conjugate of claim 1, corresponding to the structure:

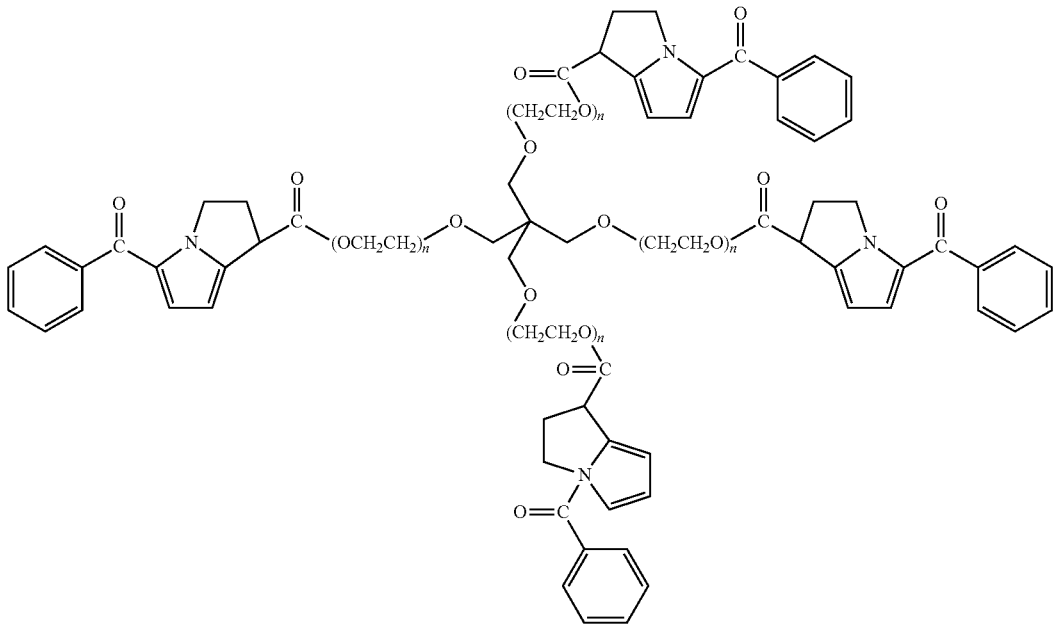

wherein the weight average molecular weight of the polymer in the conjugate is from 500 daltons to 100,000 daltons.

* * * * *

UNITED STATES PATENT AND TRADEMARK OFFICE
CERTIFICATE OF CORRECTION

PATENT NO. : 8,728,493 B2  
APPLICATION NO. : 11/454998  
DATED : May 20, 2014  
INVENTOR(S) : Kevin Burton et al.

Page 1 of 1

It is certified that error appears in the above-identified patent and that said Letters Patent is hereby corrected as shown below:

On the title page, item (54) and in the specification, column 1, in the Title, "POLYMER BASED" should be changed to --POLYMER-BASED--.

In the Claims  
Column 49, lines 65-66, in Claim 6, Line 1, "polyethylene glycol)" should be changed to --poly(ethylene glycol)--.  
Column 50, lines 5-6, in Claim 7, Line 1, "polyethylene glycol)" should be changed to --poly(ethylene glycol)--.

Signed and Sealed this  
Twenty-eighth Day of April, 2015

Michelle K. Lee  
*Director of the United States Patent and Trademark Office*

UNITED STATES PATENT AND TRADEMARK OFFICE
CERTIFICATE OF CORRECTION

PATENT NO. : 8,728,493 B2  
APPLICATION NO. : 11/454998  
DATED : May 20, 2014  
INVENTOR(S) : Kevin Burton et al.

Page 1 of 1

It is certified that error appears in the above-identified patent and that said Letters Patent is hereby corrected as shown below:

In the Claims

In Claim 16, the chemical structure should appear as follows:

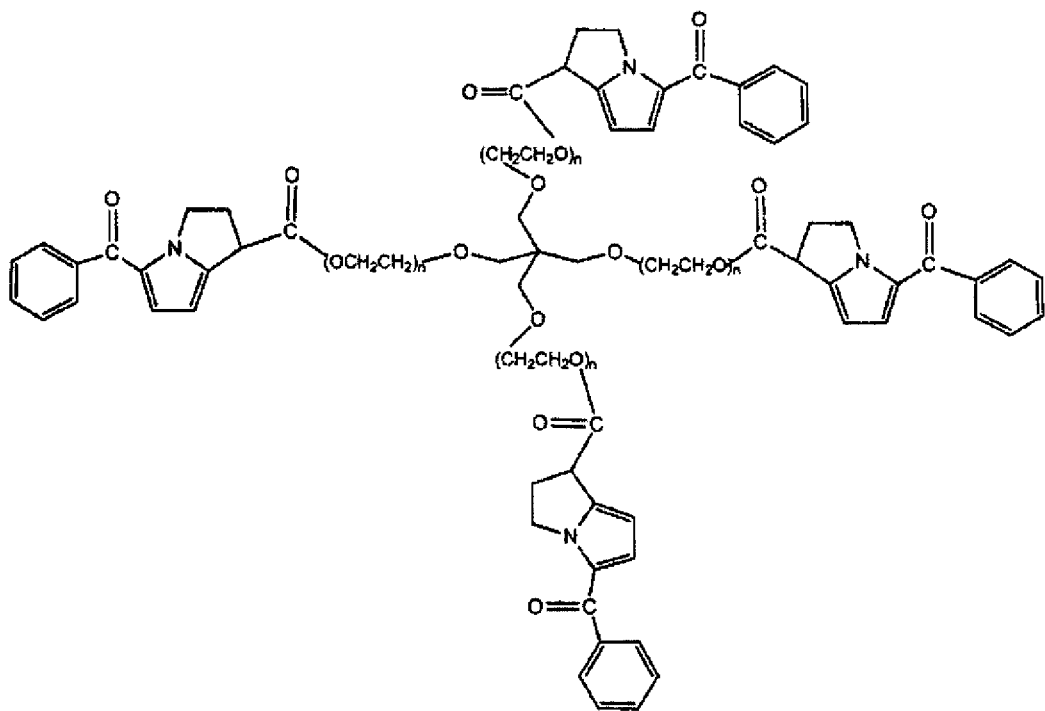

Signed and Sealed this  
Second Day of June, 2015

Michelle K. Lee  
*Director of the United States Patent and Trademark Office*